(12) United States Patent
Ellis

(10) Patent No.: US 7,036,800 B2
(45) Date of Patent: May 2, 2006

(54) AUTOMATICALLY CONTROLLING THE INTERACTION OF A MEDIUM WITH AN EXTERNAL ENVIRONMENT

(76) Inventor: Earle R. Ellis, 108 Melvins End, Yorktown, VA (US) 23693

( * ) Notice: Subject to any disclaimer, the term of this patent is extended or adjusted under 35 U.S.C. 154(b) by 92 days.

(21) Appl. No.: 10/408,380

(22) Filed: Apr. 7, 2003

(65) Prior Publication Data
US 2004/0003724 A1    Jan. 8, 2004

Related U.S. Application Data

(60) Provisional application No. 60/370,794, filed on Apr. 8, 2002.

(51) Int. Cl.
*B01F 3/04* (2006.01)
(52) U.S. Cl. ............ 261/26; 261/30; 261/DIG. 88; 422/124; 239/57; 239/60
(58) Field of Classification Search ........... 261/26, 261/30, 104, DIG. 88; 422/124; 239/57, 239/60
See application file for complete search history.

(56) References Cited

U.S. PATENT DOCUMENTS

| | | | | |
|---|---|---|---|---|
| 3,948,445 A | * | 4/1976 | Andeweg ............ | 239/53 |
| 5,029,729 A | * | 7/1991 | Madsen et al. ........ | 222/1 |
| 5,924,597 A | * | 7/1999 | Lynn ................ | 222/1 |
| 6,032,930 A | * | 3/2000 | Calino .............. | 261/26 |

* cited by examiner

Primary Examiner—Robert A. Hopkins
(74) Attorney, Agent, or Firm—George F. Helfrich

(57) ABSTRACT

A device is presented which automatically controls the interaction of a medium with an external environment, the temperature of which varies or remains constant. In addition to the medium, the device includes a mechanism for providing constant effectiveness of the medium in the external environment, and an automatic drive mechanism which drives the mechanism for providing constant effectiveness of the medium in the external environment. Advantageously, the device includes a receptacle for the medium, and the receptacle includes a housing incorporating the mechanism for providing constant effectiveness of the medium in the external environment, which is beneficially a movable vent or an expandable vent. The automatic drive mechanism is advantageously a temperature-responsive member or a temperature-responsive fluid movement device. The temperature-responsive member, which manifests variations in the surface area thereof as the temperature thereof is raised, is beneficially one of the following: a linear spring, a spiral metallic spring, a multi-metallic spring, a polymeric spring, or a pop spring. A preferred embodiment of the device includes at least one static vent positioned within the housing in alignment with at least one movable vent positioned therein, and the at least one movable vent is driven by the automatic drive mechanism to move in relation to the at least one static vent, thereby providing constant effectiveness of the medium in the external environment by affording varying exposure thereof as the temperature of the external environment varies.

27 Claims, 20 Drawing Sheets

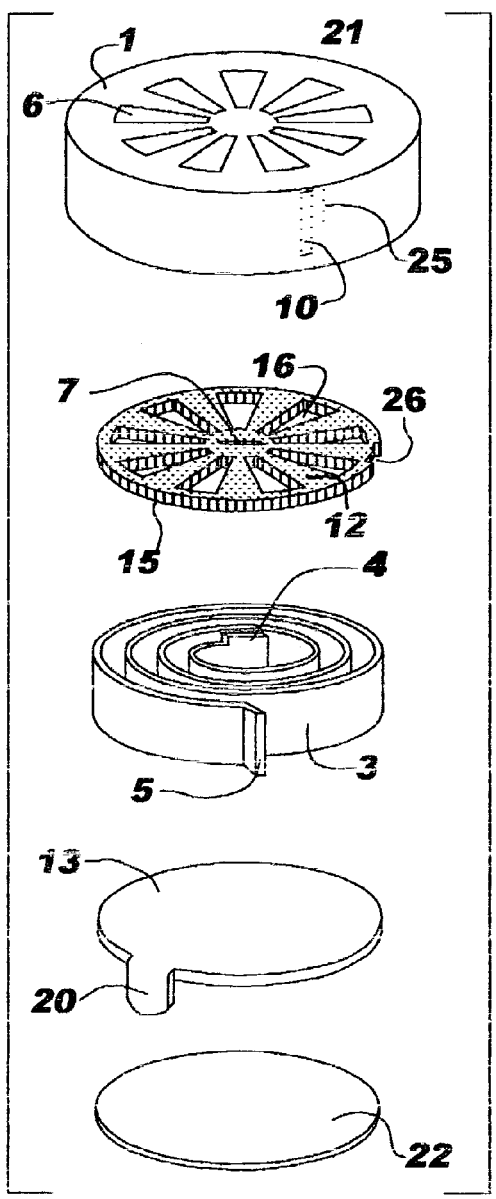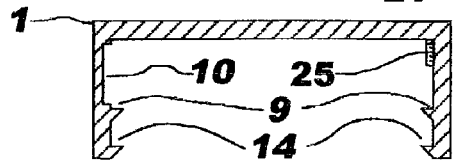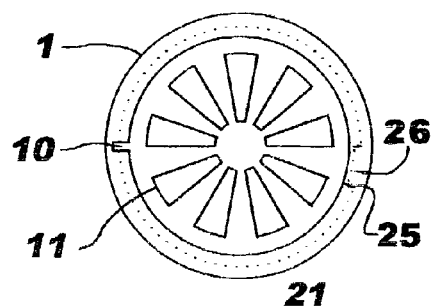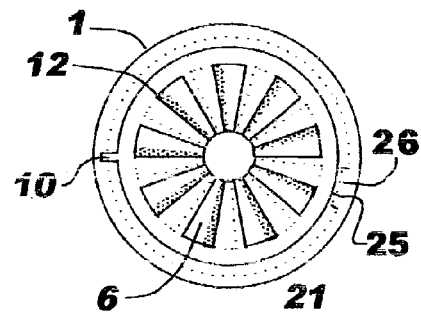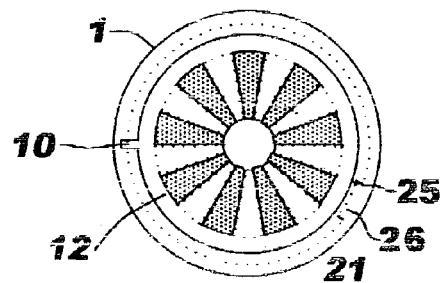

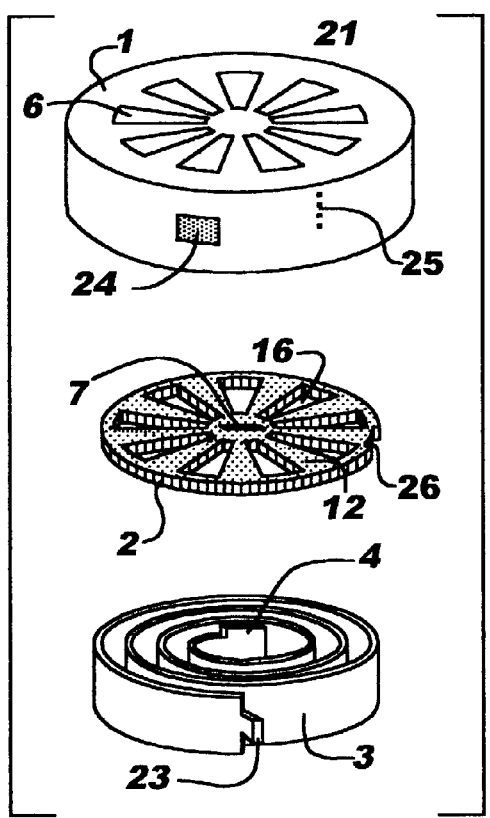
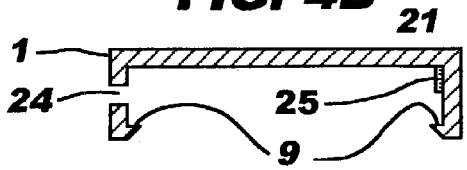
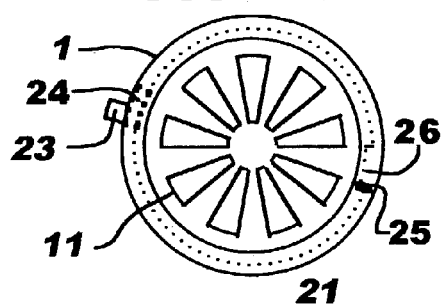
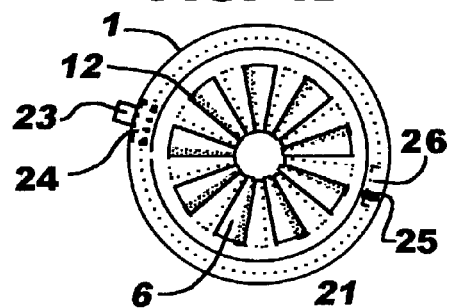
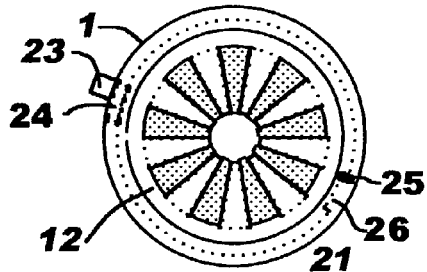

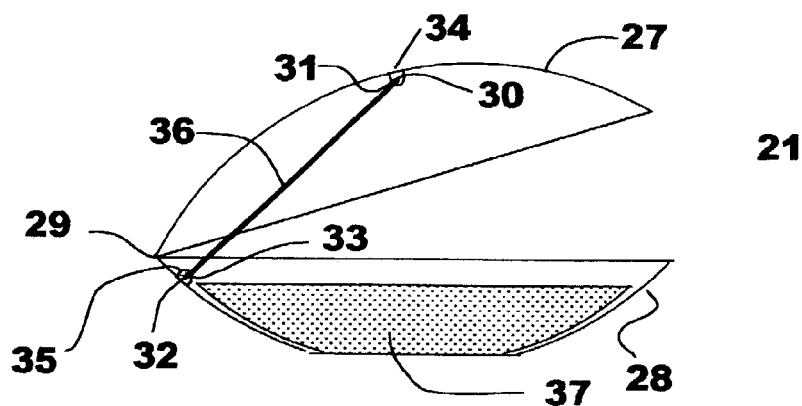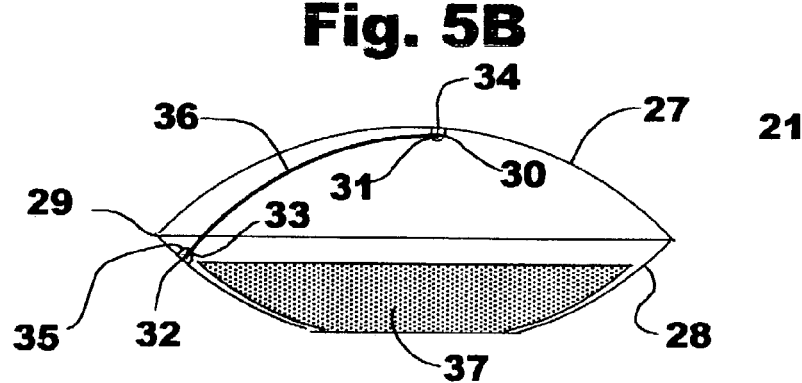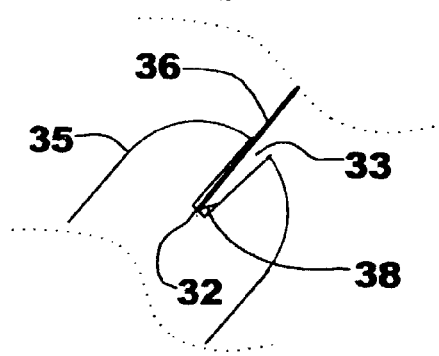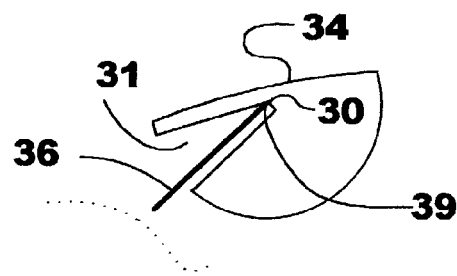

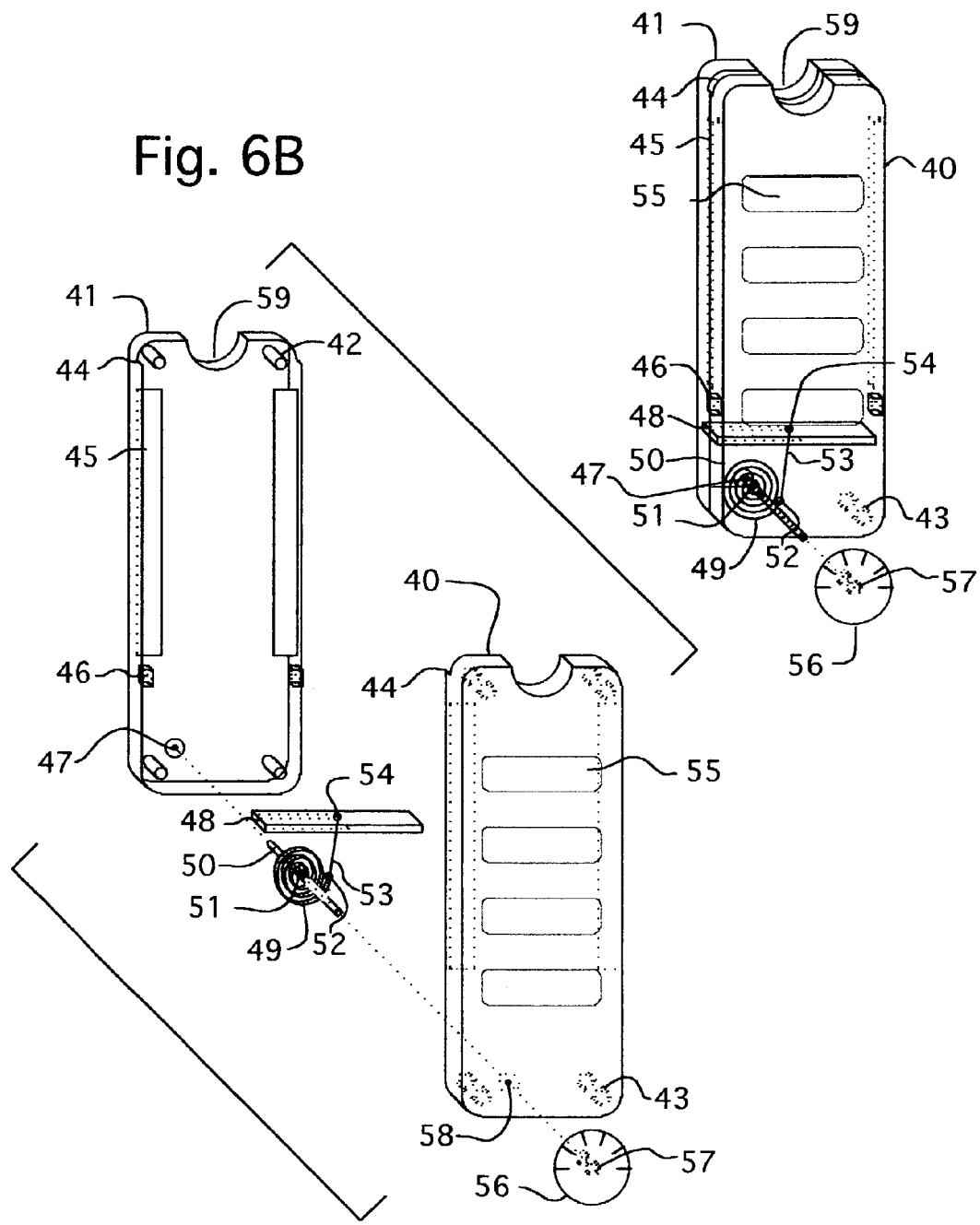

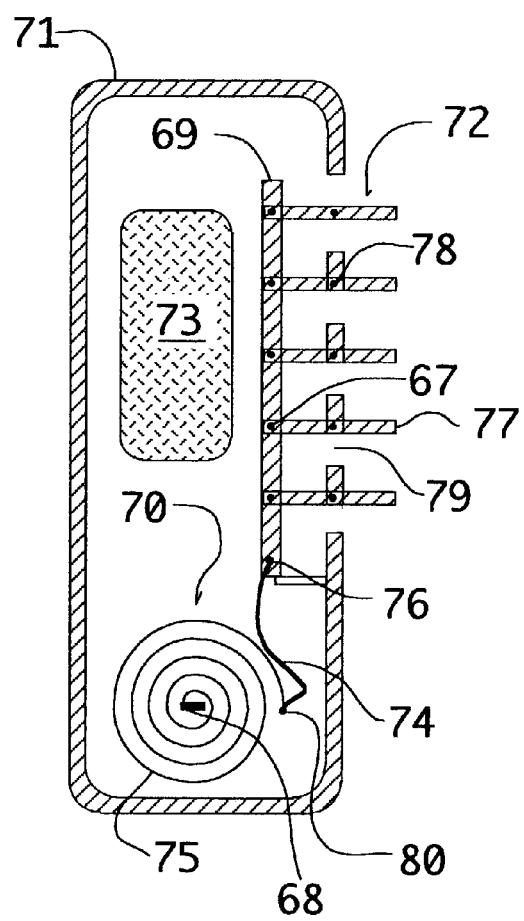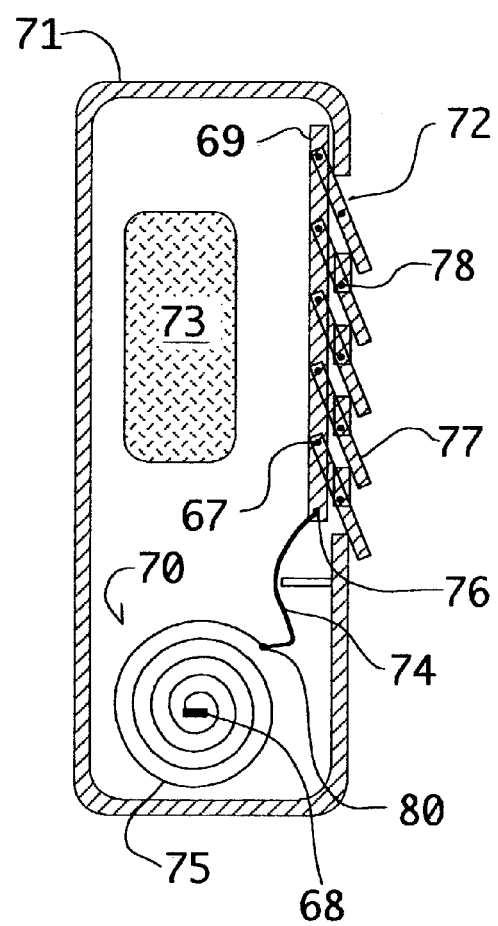

FIG. 11
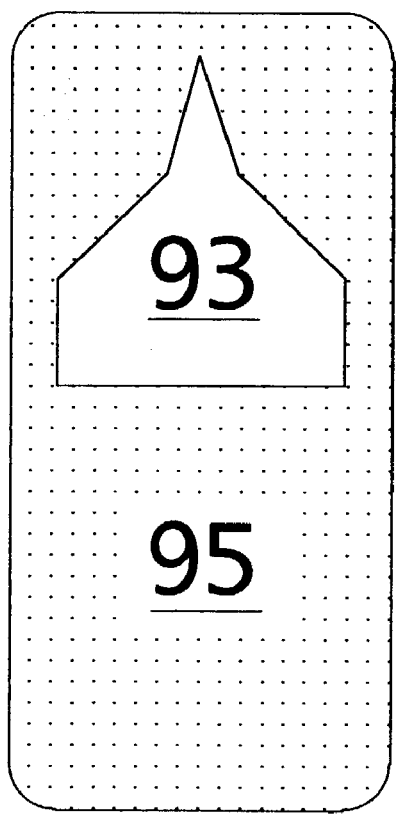
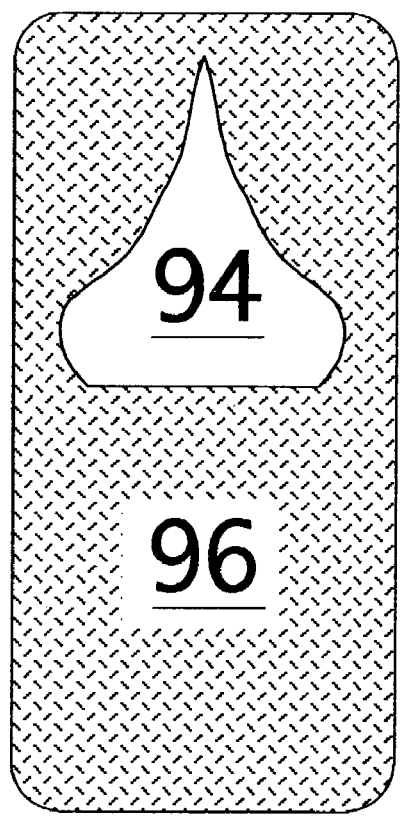

FIG. 12A
FIG. 12B
FIG. 12C
FIG. 12D
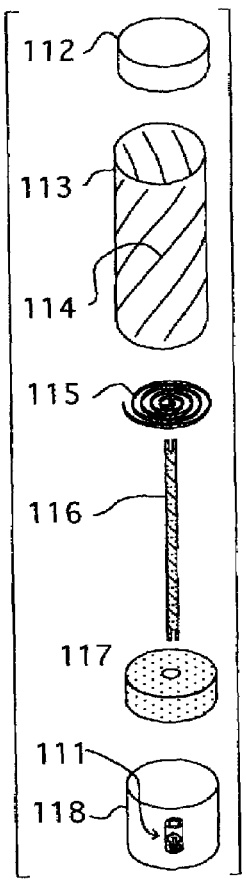
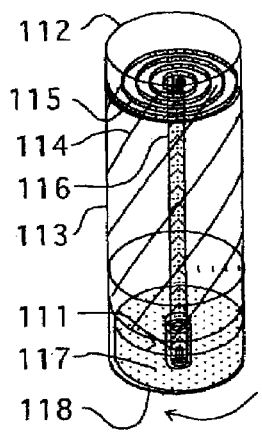
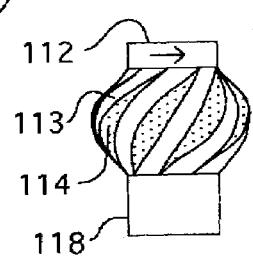
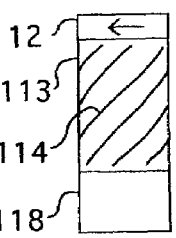
FIG. 12E
FIG. 12F
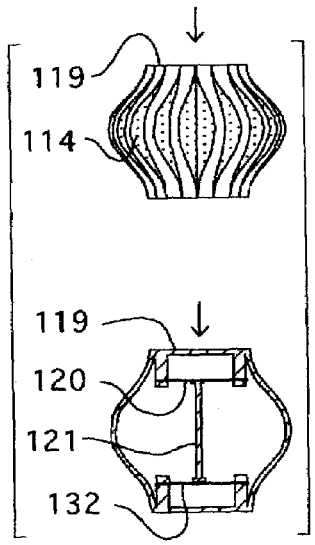
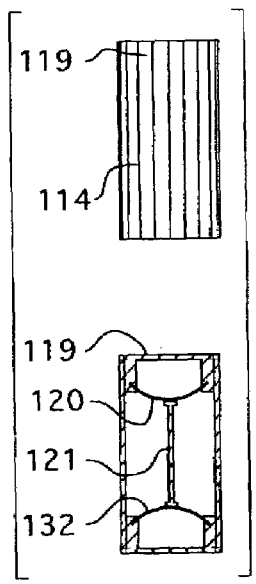

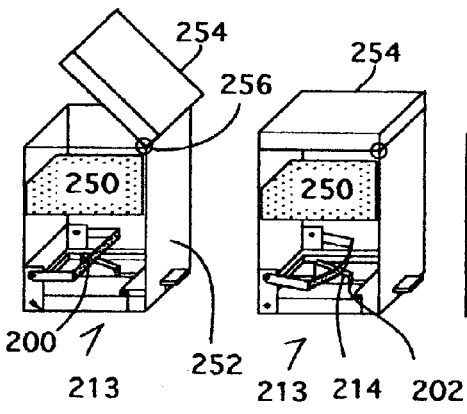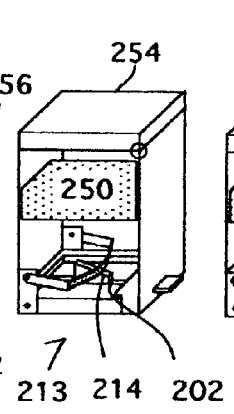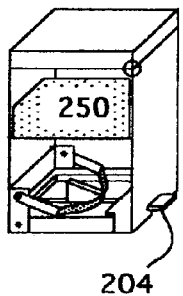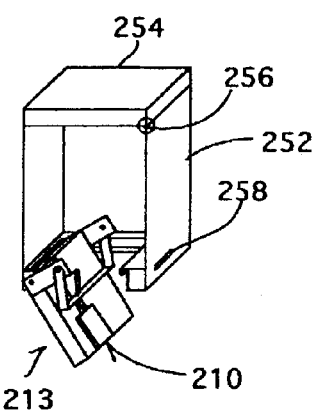
Fig. 22A  Fig. 22B  Fig. 22C  Fig. 22D
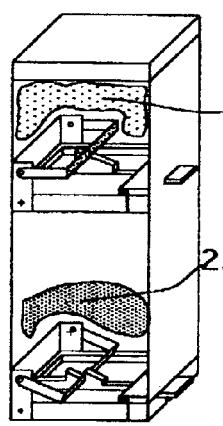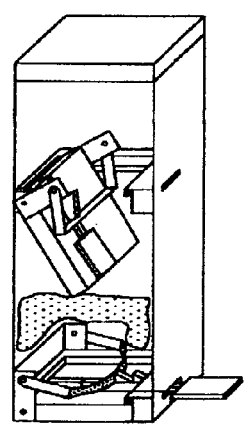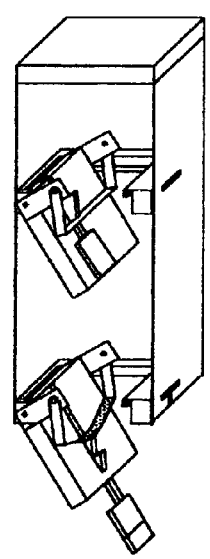
Fig. 23 A  Fig. 23 B  Fig. 23 C

US 7,036,800 B2

AUTOMATICALLY CONTROLLING THE INTERACTION OF A MEDIUM WITH AN EXTERNAL ENVIRONMENT

CROSS-REFERENCE TO RELATED PATENT APPLICATION

This application claims the benefit of U.S. Provisional Application No. 60/370,794 filed Apr. 8, 2002.

BACKGROUND OF THE INVENTION

1. Field of the Invention

This invention relates generally to the interaction of a medium with its external environment. It relates particularly to a device for automatically controlling the interaction of a medium with its external environment.

2. Description of the Related Art

The interaction of a medium with its external environment has occupied the attention of many innovators over a considerable period of time, especially in the recent past and continuing through the present day. For example, a number of devices for modifying air quality have appeared and continue to appear on the market. These devices, which volatilize and dispense a medium, such as an air freshener, into a room or automobile interior, are often the subject of Unites States Patents. Exemplary of such United States Patents are the following: U.S. Pat. Nos. 6,361,752; 6,123,935; 6,141,496; 6,514,467; 6,416,043; 6,267,297; 6,103,201; 5,932,147; 5,253,804; and 4,754,696. Howsoever efficacious, these devices are found wanting in that they do not provide for automatic control of the interaction of the medium with the external environment, the temperature of which is often variable, not do they provide constant effectiveness of the medium in the external environment is afforded. Furthermore, presently available devices do not provide for automatic control of the interaction of a medium, and the constant effectiveness thereof with an external environment, when the desired interaction is something other than volatilizing and dispensing—that is to say, absorbing, absorbing and chemically reacting, among other interactions, are not provided for.

SUMMARY OF THE INVENTION

It is accordingly a primary object of the present invention to obviate the disadvantages of the related art. This object is achieved, and attending benefits are obtained, by the provision of the present invention, which is a device for automatically controlling the interaction of a medium with an external environment the temperature of which varies or remains constant. The device includes a medium, which is one or more of the following: a temperature-sensitive medium, a moisture-sensitive medium, a chemically-reactive medium, an evaporative medium, and an absorptive medium. The medium can be a liquid, solid, gas, fiber, gel, or an encapsulated material. The instant device also includes a mechanism for providing constant effectiveness of the medium in the external environment, as well as an automatic drive mechanism, which communicates with and drives the mechanism providing constant effectiveness of the medium in the external environment, so that a desired interaction of the medium with the external environment is afforded.

The instant drive mechanism advantageously includes a container for the medium, which is preferably a receptacle having a housing which incorporates the mechanism for providing constant effectiveness of the medium in the external environment, which is beneficially a movable vent or an expandable vent. The movable vent is preferably one or more of the following: a movable shutter, a movable louver, a movable orifice, and a movable sheath. The automatic drive mechanism, which communicates with and drives the mechanism for providing constant effectiveness of the medium in the external environment, is advantageously a temperature-responsive member or a temperature-responsive fluid movement device. The temperature-responsive member, which manifests variations in the surface area thereof as the temperature thereof is varied, is preferably a linear spring, a spiral metallic spring, a multi-metallic spring, a polymeric spring, or a pop spring.

Excellent results are obtained if the device of the present invention also includes a static vent, which is securely positioned within the housing in substantial alignment with a movable vent, and the movable vent is driven by the automatic drive mechanism to move relative to the static vent, so that constant effectiveness of the medium in the external environment is provided by varying the exposure of the medium in the external environment. The static vent is advantageously a static orifice, a static louver, or a static sheath. Especially beneficial results are achieved for some media if the movable vent and the static vent have essentially the same geometric shapes, so that constant effectiveness of the medium in the external environment is achieved by varying the exposure of the medium to the external environment in a substantially linear fashion. Especially beneficial results are also achieved for some media in the movable vent and the static vent has essentially different geometric shapes, so that constant effectiveness of the medium in the external environment is achieved by varying the exposure of the medium to the external environment in a substantially non-linear fashion.

Additional preferred embodiments of the device according to the present invention includes a device having a cooperating mechanism for presenting an on/off condition at chosen levels of exposure of the medium to the external environment, as well as a device having a cooperating mechanism for inducing a temperature change in the medium, the latter mechanism being advantageously a programmable heater such as a thermal profile generator or a time/temperature thermal profile generator. When a programmable heater is employed, beneficial results are obtained if the mechanism is provided to cooperate with the programmable heater and present a signal evincing the end of a programmed cycle.

Additional preferred embodiments of the device according to the present invention includes a mechanism for inducing air currents across the medium contained in the receptacle. Such a mechanism for inducing air currents is preferably a fan programmed for continuous operation at a substantially constant blade speed, or a fan the blade speed of which is controlled by the automatic drive mechanism.

In another preferred embodiment, the device according to the present invention has a housing which includes a front face and a back face, which are joined together to form a slot therebetween. The slot functions as the reservoir for the medium, which is configured in the form of a sheet having two major surfaces. The sheet is configured to fit within the slot and is capable of movement therein. At least one of the front face and the back face of the housing has at least one fixed vent therein. A temperature responsive member, which serves as the automatic drive mechanism, is connected to a holder for medium, which moves the medium within the slot as a result of changes in temperature, so that the medium is oriented with respect to the at least one vent for communication therethrough with the external environment. The major surfaces of the medium have at least one masked area and at least one unmasked area thereon, each masked and unmasked area having substantially the same shape and surface area as the at least one fixed vent. The at least one masked area is in substantial alignment with the at least one fixed vent when the external environment is at a first temperature, and the at least one unmasked area is in substantial alignment with the at least one fixed vent when the external environment is at a second temperature, the first temperature being higher than the second temperature.

Yet another preferred embodiment of the present invention is a device having a housing which includes a first concave face and a second concave face, which faces when joined together form an integral, hollow enclosure. The first concave face and the second concave face are connected together at one area thereof on one edge thereof by means of a hinge. The second concave face contains the medium therein. The automatic drive mechanism is a bimetallic spring, which is attached to the first concave face and the second concave face, respectively, in the vicinity of the hinge. The first and second concave faces are positioned apart to expose the medium to the external environment when the external environment is at a first temperature, and the first and second concave faces are drawn together by means of the bimetallic spring to form an integral hollow enclosure when the external environment is at a second temperature, the first temperature being lower than the second temperature.

Yet another preferred embodiment of the present invention is a device having a housing for the receptacle for the medium, and an automatic drive mechanism which is a temperature-responsive member such as a spring. For this embodiment the external environment is a liquid, and the medium is a liquid or a powder which is contained in the receptacle. In this embodiment the device additionally includes a mechanism for automatically dispensing the medium from the receptacle into the liquid external environment, which mechanism for automatically dispensing the medium is driven by the automatic drive mechanism.

BRIEF DESCRIPTION OF THE DRAWINGS

For a more complete understanding of the present invention, including its primary object and attending benefits, reference should be made to the Detailed Description of the Invention, which is set forth below. This Detailed Description should be read together with the accompanying drawings, wherein:

FIGS. 2A, 2B, 2C, 2D, and 2E depict a second preferred embodiment of the present invention in schematic representations, including exploded perspective, sectional, and top views thereof, respectively.

FIGS. 4A, 4B, 4C, 4D, and 4E depict a fourth preferred embodiment of the present invention in schematic representations, including exploded perspective, sectional, and top views thereof, respectively.

FIGS. 5A, 5B, 5C, 5D depict a fifth preferred embodiment of the present invention in schematic representations, including side views and detailed views thereof, respectively.

FIGS. 6A, 6B, depict a sixth preferred embodiment of the present invention in schematic representations, including a perspective and exploded perspective view thereof, respectively.

FIGS. 9A and 9B schematically depict in sectional representation a seventh preferred embodiment according to the present invention.

FIG. 11 schematically represents two asymmetric profiles for vents which are employed in preferred embodiments according to the present invention.

FIGS. 12A, 12B, 12C, 12D, 12E and 12F schematically depict a ninth preferred embodiment according to the present invention.

FIGS. 21A, 21B, 21C, 21D, and 21E are schematic representations illustrating the operation of the thermal response housing assembly of FIGS. 20A–20B.

FIGS. 22A, 22B, and 22C 22D are schematic representations of a seventeenth preferred embodiment of the present invention, which is a closely related to the sixteenth preferred embodiment represented in FIGS. 19A–19D.

FIGS. 23A, 23B, and 23C are schematic representations of an eighteenth preferred embodiment of the present invention.

DETAILED DESCRIPTION OF THE INVENTION

Figure 1A:
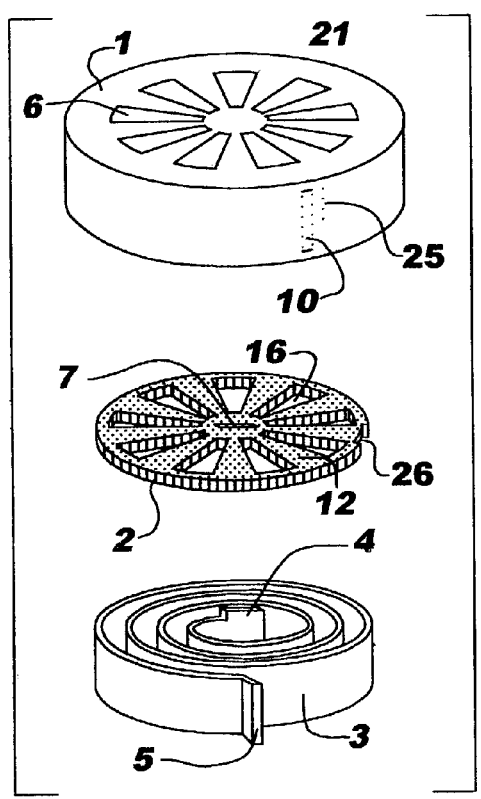
FIGS. 1A, 1B, 1C, 1D, and 1E depict a first preferred embodiment of the present invention in schematic representations, including exploded perspective, sectional, and top views thereof, respectively.
Figure 1B:
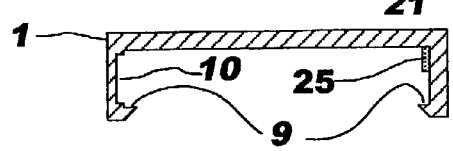

Referring now to the drawings in detail, FIG. 1A illustrates the most basic configuration of the embodiments. The automatically controlled device comprises only three pieces: an outer housing with static vents (hereafter referred to as housing) 1, a medium 2, which is shaped into a movable shutter 2 (hereafter, the medium and shutter will be used interchangeably, contingent on the explanation needed) and a spring 3.

Vent is defined as the group consisting of louvers, orifices, sheaths, and other geometrical openings that allow the medium to communicate with its external environment.

In a preferred embodiment, the spring has an unrestrained end 4 and a stationary end 5. The shutter 2 serves two purposes: it functions as the medium and the shutter 2. The shutter 2 comprises multiple movable vents 16 that are equally spaced circumferentially and a centrally located unrestrained spring end attachment hole 7.

The shutter 2 for this application is comprised of a member of the group of homogeneous, non-homogeneous, multi-layered and combined materials.

An example of a homogeneous material would be naphthalene and is used as the active and medium 2. Naphthalene is used for mothballs. This material is molded into the shape of a shutter 2.

An example of a non-homogeneous material is an active, impregnated into a carrier material, such as cardboard, plastic, or compressed sawdust. The shutter 2 is made of a mixture of cardboard particulates, plastic and active and molded into or impregnated into the shape of a shutter 2. The plastic acts as the binder and the cardboard is used to absorb and disperse the active. The example of an active in this case is a fragrance.

An example of a layered or laminated structure is a medium comprising progressive layers, in any permutation, of a homogeneous layer, a non-homogeneous layer and even a layer where the active is encapsulated by a plastic coating (e.g. microspheres).

The shutter medium 2 is placed onto the unrestrained end of the spring 4 via the centrally located spring attachment hole 7. The spring and shutter assembly is inserted into the housing 1 until the assembly passes through, snaps in, and sits onto the spring and shutter assembly retainers 9. The shutter assembly is then rotated until the stationary end of the spring 5 snaps into the spring retaining slot 10. Once the entire assembly is complete, the device is functional.

Figure 1C:
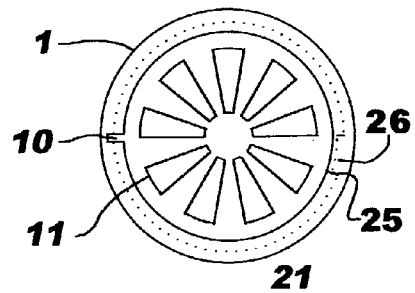
Figure 1D:
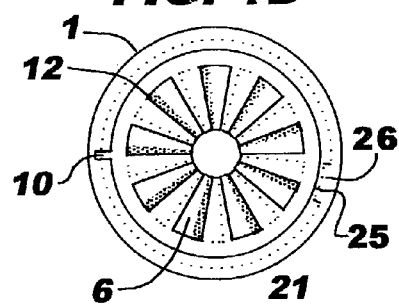
Figure 1E:
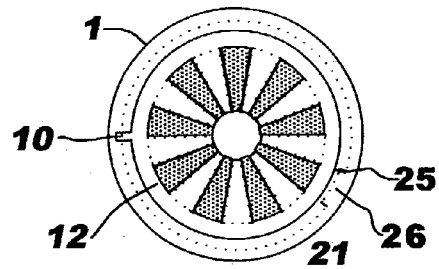
Figure 3A:
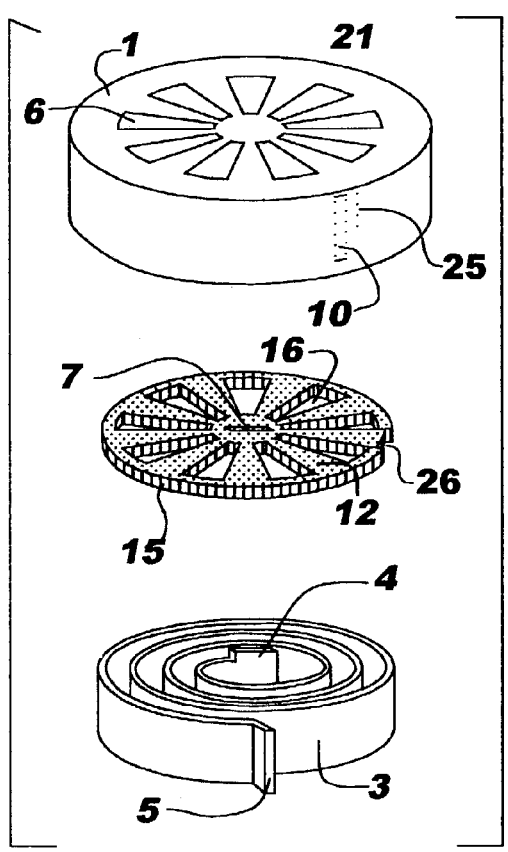
FIGS. 3A, 3B, 3C, 3D, 3E and 3F depict a third preferred embodiment of the present invention in schematic representations, including exploded perspective, sectional, top views, and a section view thereof, respectively.
Figure 3B:
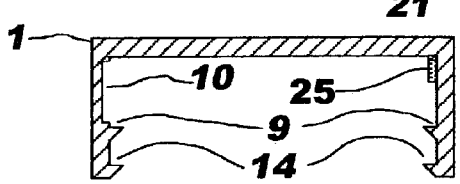
Figure 3C:
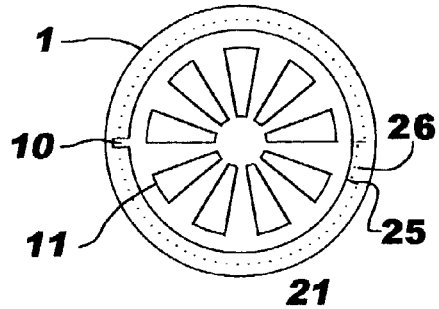
Figure 3D:
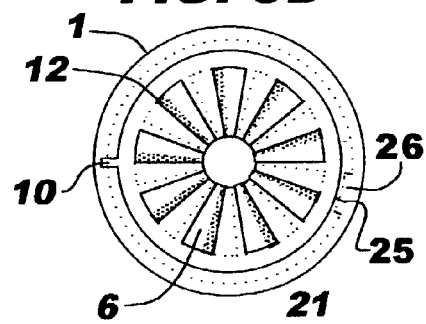
Figure 3F:
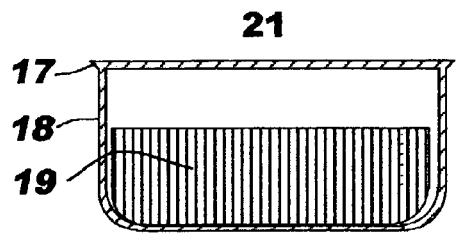
Figure 3E:
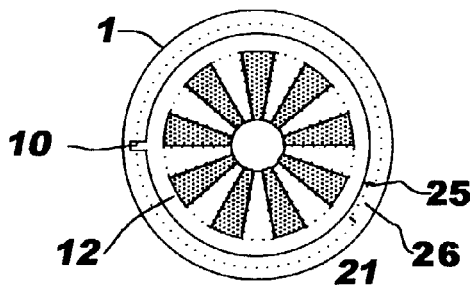

The changes in ambient temperature control the rotation and alignment of the shutter vents 16 to the static vents 6. The device is set so that when the ambient temperature increases or decreases, the shutter vents 16 and the static vents 6 can either be totally aligned, misaligned or any configuration in between. In this preferred embodiment, when the ambient temperature reaches its maximum designed temperature, the shutter vents 16 and the static vents 6 are in total alignment FIG. 1C at 11 and minimal medium 2 is exposed to the external environment 21. This occurs because both the static vents 6 and the shutter vents 16 have substantially the same geometric shapes. When the device reaches its lowest designed temperature, the static vents 6 and shutter vents 16 are in total misalignment, thereby exposing the maximum amount of medium FIG. 1E at 12 through the static vent 6 and into its external environment 21.

FIGS. 2A–2E illustrate a four-piece device that comprises a housing 1, a shutter 15, a spring 3, and a medium 13.

The device functions similar to the device in FIG. 1A, with two exceptions: the shutter 15, although identical in design to the medium FIG. 1A at 2, does not serve the purpose as the medium 13. The medium 13 is a separate refillable item.

The device is assembled in the same manner as the device in FIG. 1A, with the exception that the shutter assembly is now inserted into the housing 1 until it snaps into and comes to rest on the shutter assembly retainers 9. The shutter assembly is then rotated until the stationary spring end 5 snaps into the spring retaining slot 10.

The medium 13 has an extended pull-tab 20 to aid in insertion and removal of the medium 13. The medium 13 is ultimately inserted into the housing 1 until it snaps into and comes to rest upon the medium retainers 14.

A medium barrier 22 has been added to the back of the medium 13 to act as a barrier 22 so that the face of the medium 13 will only communicate with its external environment 21 through the shutter vents 16 and the static vents 6. This forces the medium 13 to communicate with its external environment 21 solely through the automatic control system of the device.

The shutter's 15 only function in FIGS. 2A–2E is to change the amount of exposure and the degree to which the medium 13 is allowed to communicate with its external environment 21. As the temperature changes, the non-restricted spring end 4 rotates thereby causing the shutter 16 to align or misalign with the static vent 6.

In this preferred embodiment, increasing ambient temperatures will cause the spring 3 to expand and rotate the shutter 15 counterclockwise until the shutter vents 16 are in total misalignment with the static vents 6. This creates the situation where the static vents 6 are totally blocked off by the interference of the areas of the shutter that are non-vented 12 and results in virtually no communication of the medium 13 with its external environment 21.

The opposite result occurs when the ambient temperature decreases. The spring 3 contracts and causes the shutter 15 to rotate clockwise. As the shutter vents 16 become increasingly more aligned with the static vents 6, perfect alignments are ultimately achieved between the static vents 6 and the shutter vents 16. In this configuration, the shutter 15 creates no restriction of the static vents 6. This is depicted in FIG. 2C at 11. This configuration allows the medium 13 to communicate fully and maximally with its external environment 21.

This preferred embodiment and the way in which the shutter 15 rotates is ideal for a fragrance medium. Fragrances exposed to high ambient temperatures typically exhibit high vapor pressures and evaporation rates. This results in a high level of perceived fragrance strength by the consumer if left uncontrolled. The opposite is true if the fragrance medium is subject to low ambient temperatures. The consumer perceives the fragrance strength as weak or insufficient if left uncontrolled. Ideally, the perceived strength of the fragrance would be linear and independent of temperature. This device does just that; it removes the external variable of temperature variation on the medium 13 by automatically controlling the degree to which the medium is allowed to communicate with its external environment 21 throughout its useful temperature range. This is determined by the degree that the non-vented shutter areas 12 block off the static vents 6 in response to temperature change. In this preferred embodiment, the shutter 15 increases the exposure and communication of the medium 13 to its external environment 21 when the temperature decreases, by progressively minimizing the degree to which it blocks off the static vents 6. It also progressively decreases the blockage of the static vents 6 as the temperatures rises. The result is the device increases the exposure of the medium 13 to its environment 21 when the fragrance is perceived as being weak and ineffective and decreases the exposure or communication of the medium 13 to its surroundings 21 when the fragrance is perceived as too strong or overpowering. The progression of how the shutter controls the ability of the medium 13 to communicate with its external environment 21 is depicted in FIG. 2C, FIG. 2D, and FIG. 2E. FIG. 2C shows the static vents 6 and the shutter vents 16 in total alignment 11. FIG. 2D shows the shutter 15 beginning to close. The non-vented shutter area 12 is partially blocking off the static vent 6. FIG. 2E shows the static vent 6 totally blocked off by the non vented shutter area 12. The automatic rotation of the shutter 15 with changing temperature, linearizes the perceived strength of the fragrance with changing temperatures and therefore blocks out the external temperature variable the fragrance is affected by and exposed to.

It must be noted that the spring 3 can be turned over. It will then rotate in the opposite direction and move clockwise with increasing temperatures and counterclockwise with decreasing temperatures. It accomplishes the opposite results and increases the exposure of the medium 13 when hot and decreases the exposure of the medium 13 when cold. This design set up is useful for controlling and optimizing the efficacy of various insect control media; such as pheromones, insecticides, and repellants when insects are most active (hot weather) and requires the maximum amount of medium 13 exposure and helps prolong the useful life of the medium by blocking of exposure of the medium 13 to its external environment when the insects are not active. This set up is also useful for absorptive medium types.

FIGS. 3A–3E illustrate a five-piece device, which includes a hosing 1, a shutter 15, a spring 3, a reservoir 18, and a medium 19.

The device in FIGS. 3A–3E is assembled in the same manner as the device in FIGS. 2A–2E with the exception of adding and affixing a reservoir containing the medium 18 instead of just the medium itself FIG. 2A at 13. The reservoir 18 is installed by inserting it into the housing 1 until the lip on the reservoir 17 snaps into and comes to rest on the reservoir retainer's 14. The device functions, in all aspects, identically to the device in FIG. 2A.

FIGS. 4A–4E illustrates a device comprising three-pieces: a housing 1, a medium acting as a shutter (hereafter referred to as the shutter) 2 and a manually adjustable spring 3.

The housing 1 is comprised of static vents 6, a spring adjustment-retaining slot 24 and a shutter rotation limiter tab 25. The spring adjustment retaining slot 24 is required to retain the spring adjuster tab 23 and allow enough lateral movement of the spring-adjuster tab 23 to move the medium 2 to the desired position in relation to the static vents 6. The shutter rotation stop tab 25 cooperating with the shutter rotation stop slot 26 is required to insure the shutter doesn't travel beyond its intended maximum and minimum distances of travel. In essence, the spring is not allowed to over travel its design limits. If the device was designed to expose no medium to the external environment at 120 F, the shutter stop 25 inhibits the shutter from rotating beyond the desired alignment of the shutter vents 16 to the static vents 6. In this case, perfect alignment of the vents would expose no medium to the environment and satisfy the desired effect. However, without the stops 25, the shutter 2 will continue to rotate, as temperatures greater than the 120 F design temperature are present. This will actually begin to expose the medium to the environment again, even though it would be highly undesirable. The same is true for minimum designed temperatures. Once the lowest design temperature is present, the maximum amount of medium 2 is exposed to the environment 21 and further decreases in temperature will have no affect on the ability of the shutter to rotate; the shutter rotation stop 25 insures this.

When the consumer desires to vary the amount of medium 2 exposed to the external environment 21, the consumer will move the manual spring-adjuster tab 23 left or right.

In a preferred embodiment, and using a fragrance medium as an example, the consumer would move the spring-adjusting tab 23 clockwise (right) to reduce the exposure of the medium to its environment 21 if the consumer perceived the fragrance strength as being too strong and counter clockwise to expose more of the medium 2 if the fragrance strength was perceived as being too weak. It must be noted, that the manual spring adjuster 23 concept may be used in many of the following devices as well, to set or vary an infinite amount activation temperatures within the useful temperature range, simply by preloading or unloading the spring. This would be done to satisfy the needs of specific applications.

Once the consumer moved the spring adjuster tab 23 to the desired setting, the automatic features of the device would take over again, at the new set point, and continue to automatically compensate for variations in ambient temperature. The manual adjustment feature is desirable to the consumer because it allows the consumer to personally tailor the device to individual needs, preferences, and specific applications.

The device is installed in the same manner as the device in FIG. 1A with the exception that the spring 3 needs to be manually compressed to give the spring adjuster tab 23 the clearance necessary to be inserted into the housing 1 and snap into and come to rest on the spring assembly retainers 9. Once located on the spring assembly retainers 9, the spring assembly is rotated until the manual spring adjuster tab 23 pops through the spring adjuster-retaining slot 24. The device is now assembled and ready for use.

FIG. 5A illustrates a device that comprises an upper housing 27, a lower housing 28, a hinge 29, a medium 37, and a bimetallic spring 36.

The upper housing 27 and the lower housing 28 are connected by a hinge 29 and will be hereafter referred to as the housing assembly. The hinge is comprised of a member of the group consisting of mechanical hinges, fasteners, or integral plastic hinges.

FIG. 5D illustrates the top spring retainer assembly. The top spring retainer 34 contains a slot 31 and a top wedge hook 39 for securing the top end of the bimetallic spring 30. FIG. 5C illustrates the bottom spring retainer assembly. The bottom spring retainer 35 also contains a slot 33 and a bottom wedge hook 38 for securing the bottom end of the spring 32.

The medium 37 is contained in the lower housing 28. In this case, the lower housing 28 is acting as a medium reservoir as well.

FIG. 5A illustrates the device fully open, maximizing the exposure of the medium 37 to its external environment. Its appearance resembles an open clam shell. The device in FIG. 5A develops this configuration when the ambient temperature is the coldest and causes the bimetallic spring 30 to contract.

FIG. 5B illustrates the device fully closed, minimizing the exposure of the medium 37 to its external environment. The closure of the device is a result of high ambient temperatures expanding the spring 36 and forcing the housing assembly to close shut.

This is consistent with the previously described methods to control the perceived strength of a fragrance. When the ambient temperatures increase, the fragrance components increase in vapor pressure, evaporation rate, and perceived fragrance strength to the consumer. The opposite is true as ambient temperatures decrease. The device controls this, by opening up and allowing the medium 37 to communicate fully to its external environment when the ambient temperature is cold and the vapor pressures are at their lowest, as well as closing down, to restrict communication of the medium 37 with its external environment when the ambient temperatures get hot and the vapor pressures are at their highest.

Figure 7:
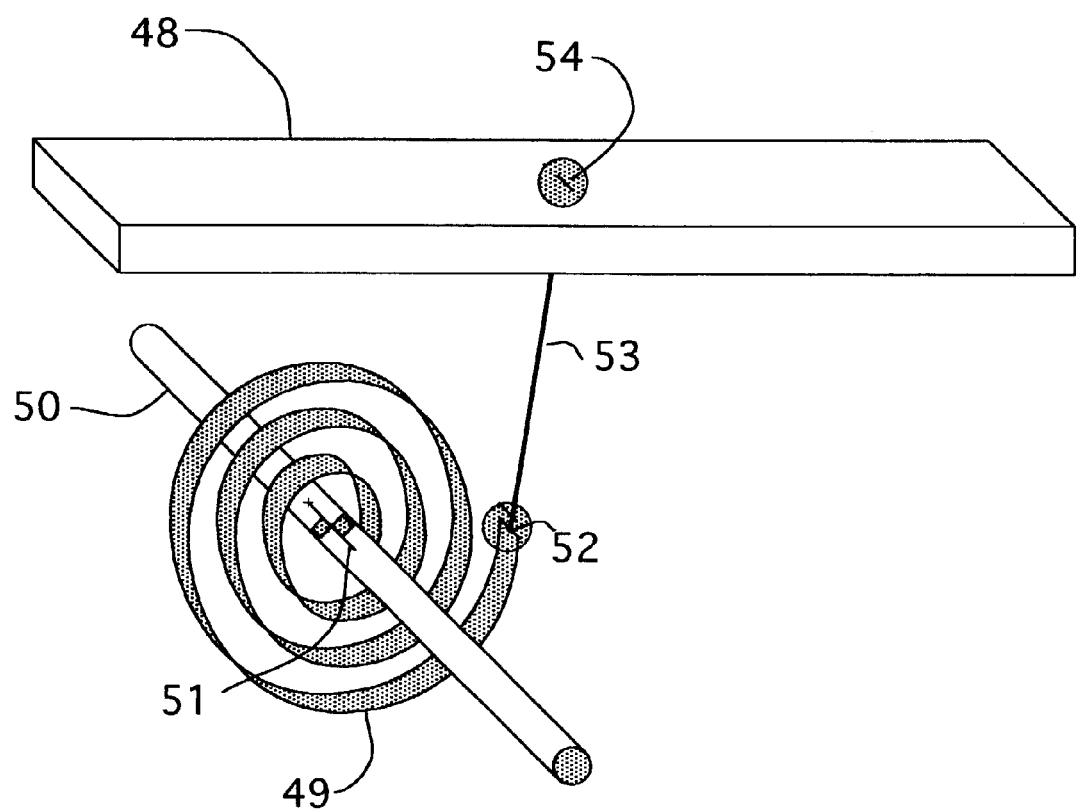
FIG. 7 schematically depicts the platform spring assembly employed in the embodiment of FIG. 6B.
Figure 8A:
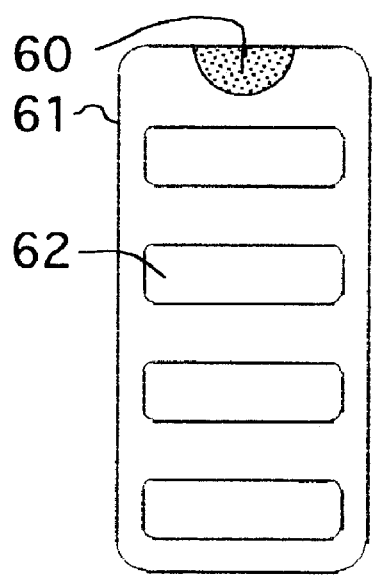
FIGS. 8A and 8B schematically depict a vented and a non-vented shutter, respectively, for employment in the embodiment of FIG. 6B.
Figure 8B:
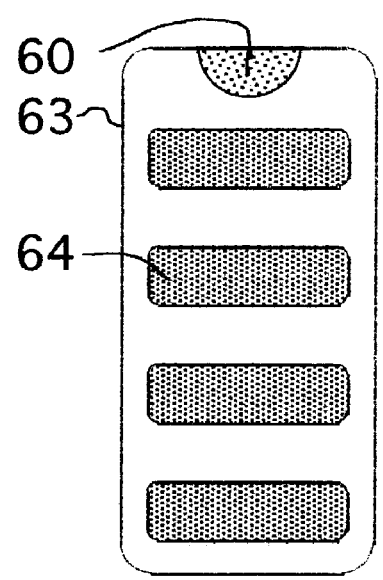

The device in FIG. 6B comprises a rear housing 41, a front housing 40, a spring assembly (FIG. 7), and a manual platform adjuster 56. The device uses two types of shutters that also function as the medium. FIG. 8A illustrates a vented shutter 61 and FIG. 8B illustrates a non-vented shutter 63 comprising masked off areas of the shutter.

The rear housing 41 comprises a shutter grip slot 59, two shutter guide rails 45, an axle-bearing slot 47, a shutter slot 44, two platform stops 46 and four front housing attachment pegs 42.

The front housing 41 comprises a shutter grip slot 59, a shutter slot 44, static housing vents 55, attachment peg receptors 43, and an axle hole 58.

The platform spring assembly (FIG. 7) comprises a spring 49, a fixed spring end anchor 51, a movable spring end pivot 52, an axle 50, a shutter platform connecting rod 53, a shutter platform 48, and a shutter platform connecting rod pivot 54.

The vented shutter in FIG. 8A at 61 has punched out holes to define the movable vents 62. The masked off shutter FIG. 8B at 63 illustrates a shutter that has the typical vent portions "masked off" with a barrier material as discussed in FIG. 2A at 22 and is designated as the masked area 64. There are no holes or vents punched in this card; the card is solid with barrier material adhered to the shutter 63 in places where vents would typically be. This creates areas where the medium cannot communicate with the external environment. It also functions as a shutter.

To begin assembling the device, the platform spring assembly housing (FIG. 7) is inserted into the rear housing 41. The front housing 40 is then appropriately assembled onto the rear housing assembly 41 via the attachment pegs 42 and the attachment peg receptors 43. Once assembled, the manual platform adjuster 56 is secured to the axle 50 via the axle receptor 57.

In a preferred embodiment using the vented shutter FIG. 8A at 61, the device functions and is used in the following manner when an evaporative medium, such as a fragrance is used. The vented shutter 61 is inserted into the grip slot 59 until the vented shutter 61 comes to rest on the platform 48. The device is designed so that the movable vents 62 and the static housing vents 55 align at the maximum design temperature. This maximally restricts the mediums communication with its external environment. When the ambient temperatures increase above the maximum design temperature, full alignment is maintained by the platform stops 46. This is important since increasing ambient temperatures would cause the spring 49 to continue to expand, resulting in the shutter 61 to over travel. If this happened, the alignment would be lost and the non-vented areas of the shutter would begin reappearing. This would start exposing the medium to its external environment again and defeat the purpose of the invention. This would cause excessive evaporation and an extremely strong and undesirable perception of the fragrance to the consumer.

The device is also designed to function in the opposite manner when the device is exposed to its lowest designed ambient temperatures. As the temperatures drops, the spring 49 continues to contract. As the spring 49 continues to contract and reaches its lowest designed temperature, the platform 48 bottoms out on the coil of the spring 49. At this point, the shutter vents 62 and the static housing vents 55 are in total misalignment. One could argue that the spring 49 would continue to contract and the spring would continue to decrease in diameter if the temperatures plummeted and thus allow the platform 48 to continue to drop. However, the additional movement is considered insignificant for the devices purpose. If an application warranted more stringent low temperature control, an added pair of stops 49 would be inserted.

The non-vented shutter FIG. 8B at 63 functions identically to the vented shutter FIG. 8A at 61. The only difference in the two shutters is that holes are not punched in the non-vented shutter 63. Barrier material is adhered or coated on the shutter and substituted for the holes or vents 62 punched in the vented shutter 61. Both methodologies accomplish the same task.

The manual platform adjuster 56 is desirable to the consumer because it allows the consumer to adjust the exposure of the medium to its external environment. Turning the manual adjuster 56 compresses or decompresses the spring 49 which ultimately control the position of the shutter 61 or 63 via the platform 48. If the consumer desires a stronger perceived fragrance, the shutter 61 or 63 is adjusted to be more misaligned with the static housing vents 55. If the consumer desires weaker fragrance strength the shutter 61 or 63 is adjusted to be better aligned with the static housing vents 55.

The device in FIGS. 9A and 9B is another automatic temperature controlled device that uses movable louvers 77 to allow the medium 73 to communicate with its external environment. The device comprises a medium 73, a housing 71, static housing vents 79, a spring rod assembly 70, and a louver assembly 72.

The spring assembly 70 comprises a spring 75, a spring static end 68, a spring rod pivot 80, and a connecting rod 74.

The louver assembly 72 comprises a louver bar 69, a louver bar pivot 76, movable louvers 77, and louver pivots 78.

In a preferred embodiment, and using a fragrance as an example of the medium 73, the device functions in the following manner. As the ambient temperature decreases, the spring 75 begins to contract and wind up. As the spring 75 contracts, it pulls the connecting rod 74 down. When this is occurring, it simultaneously causes the louvers 77 to move freely toward a horizontal position via the louver bar pivots 76, and the louver housing pivots 78. When the minimum designed ambient temperature is met, the louvers move into a horizontal position and are restricted from further travel by the louver bar stops 67. The louver bar stops 67 restrict any potential for over travel if the ambient temperature continues to drop below the lowest designed ambient temperature for the device.

The operational sequence reverses as the ambient temperature increases and approaches the device's maximally designed temperature. The spring 75 expands and unwinds; causing the connecting rod 74 to rise and simultaneously close the louvers 77 until contacting the louver housing 71 halts their movement. The louver housing 71 provides the stopping mechanism for the louvers 77 when the maximum design temperature is met.

This operational sequence is consistent with the needs of controlling the evaporative profile of a fragrance medium 73 and blocks out the temperature variable by linearizing the evaporative profile with changing temperatures. In essence, the sequence of operations increases the mediums 73 communication with its external environment as the vapor pressure or evaporation rates of the medium 73 drop off with decreasing temperatures and restricts the mediums communication with its external environment as the vapor pressure or evaporation rates climb with increasing temperatures.

Figure 10A:
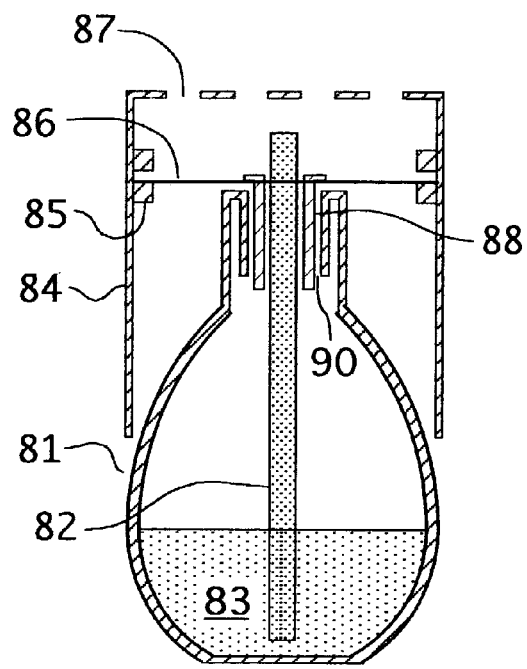
FIGS. 10A and 10B schematically depict in sectional representations an eighth preferred embodiment according to the present invention.

The device in FIG. 10A illustrates an automatic temperature controlled mechanism that comprises a housing 84, static vents 87, bimetallic spring retainers 85, a medium reservoir 81, a medium 83, a wick 82, a wick sheath 88, and a bimetallic spring 86 with a sheath retaining hole 89.

The device is assembled by inserting the sheath 88 into the sheath-retaining hole 89 and then inserting the bimetallic spring 86 into the spring retainers 85. The wick 82 is inserted into the sheath 88 and the entire assembly is inserted into the reservoir opening 90.

In a preferred embodiment, the device functions and is designed in the following manner when an evaporative medium, such as a liquid fragrance is used. Once the wick 82 is inserted into the medium 83, the medium 83 quickly saturates the wick 82 and comes to equilibrium through capillary action. The sheaths 88 main purpose is to regulate the amount of surface area the wick 82 is exposed to in relation to its external environment. Assuming the ambient temperature is held constant, exposing more of the wick 82 to its external environment increases the evaporation rate and perceived strength of the fragrance medium 83 to its external environment and ultimately the consumer. Unfortunately, ambient temperatures vary and if the wick 82 length is held constant as temperatures change, the evaporation rates and perceived strengths of the medium 83 changes. Many devices currently operate in such a fashion and are at the mercy of varying temperatures. These devices haven't blocked out the temperature variable. This device does.

Figure 10B:
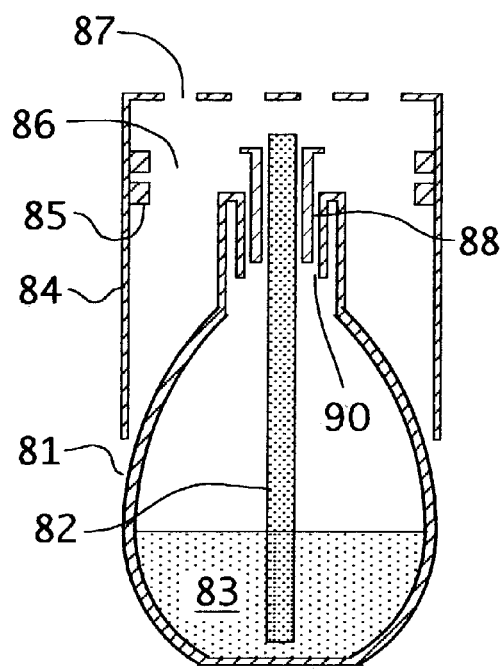
Figure 10C:
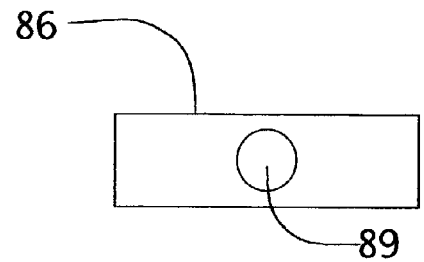

The sequence of operation is similar to what has been described previously. As the temperature increases, the bimetallic spring 86 expands and becomes increasing more convex. Since the sheath 88 is an integral part of the spring 86, the sheath 88 rises with the spring 86 and progressively reduces the surface area or length of the wick 82 exposed to its external environment. When the ambient temperature reaches the maximum design temperature of the device, the sheath 88 significantly shields the wick 82 from its external environment and only a very little portion of the wick 82 can be seen sticking out above the face of the sheath 88. This is illustrated in FIG. 10B.

FIG. 10A illustrates the device operating at its minimally designed temperature. The spring 86 is frilly contracted and the sheath 88 is allowing the maximum amount of wick 82 exposure to its external environment.

The two operating scenarios just described are consistent with the philosophy of minimizing exposure of an evaporative medium to its external environment when the ambient temperature is hot and maximizing the exposure of the medium to its surroundings when they are cold. This typically holds true for an evaporative medium, but as discussed before is opposite, if the desired outcome is to expose more of the medium 83 to its external environment when hot. To reverse the desired outcome and optimize this type of application, the spring 86 would control movement of the wick 82 instead. When the temperature increased, the wick 82 would be pulled out of the medium 83, exposing more of the wick 82 and allowing maximum communication of the medium 83 to its external environment.

FIG. 11 illustrates two asymmetric vent profiles 93 and 94. The static vent profile 93 is shown cut into a representative portion of a device housing 95. This irregular shaped vent profile 93 would be used to compensate for complex medium that exhibited up to a third order temperature response characteristic curve. The asymmetric vent 94 is shown cut into a representative portion of a movable shutter 96. This vent geometry 94 would be custom designed for a complex evaporative medium that required extremely tight control of the mediums exposure to its external environment. In essence, the more precisely the vent profile or profiles are designed to match the characteristics of a specific medium, the better the device will control the mediums constant effectiveness to its external environment throughout its useful temperature range.

The devices in FIGS. 12A–12E illustrate the operations of two expandable vent methodologies. FIG. 12A illustrates the assembly diagram for the coiled spring actuated expandable vent device FIG. 12B. The device comprises a top cap 112, an expandable vent housing 113, a coil spring 115, a spring connecting rod 116, a connecting rod anchor 111, a medium 117, and a reservoir for the medium 118.

The device is first assembled by attaching the spring 115 to the spring connecting rod 116. The medium 117 is inserted into the medium reservoir 118 and the spring connecting rod 116 is passed through the medium 117 and attached to the connecting rod anchor 111. The top cap 112 is attached to the expandable vent housing 113. The spring 115 is compressed and passed through the expandable vent housing 113 until the spring bottoms out in the top cap 112 and decompresses for a tight friction fit inside of the top cap 112 and the expandable vent housing 113 is secured to the reservoir 118.

The device functions similarly to the others previously described since the vents 114 are driven to open or close by the expansion or contraction of the spring 115. The advantage of the expandable vent device is that it allows greater than 90% medium exposure, in comparison to only 50% medium exposure that is characteristic of the movable shutter.

In a preferred embodiment of the device and assuming the medium is a fragrance, FIG. 12D illustrates the device operating at its maximally designed temperature. As the ambient temperature rises, the spring expands and rotates the vent housing 113 clockwise until it is tightly wound and the vents 114 are totally closed.

FIG. 12C illustrates the device operating at its minimally designed temperature. As the ambient temperature decreases, the spring 115 contracts and rotates counterclockwise, causing the expandable vent housing 113 to follow and open the vents 114 to their full extent.

FIGS. 12E and 12F illustrate another expandable vent device. However, this configuration of this device uses the bimetallic spring 120 as a vehicle to compress and expand the expandable vent housing 119 and hence the expandable vents 114.

FIG. 12E at 114 illustrates the device operating at its minimally designed temperature. The bimetallic springs 120 and 132 are contracted due to the exposure of a low ambient temperature. At the springs 19 and 132 contracted state, the expandable vent housing 119 is compressed and results in the expandable vents 114 bulging out. This configuration allows the medium to communicate with its external environment maximally.

FIG. 12F illustrates the device operating at its maximally designed temperature. The bimetallic springs 120 and 132 are fully expanded and cause the expandable vent housing 119 to elongate under tension. When the expandable vent housing 119 is fully elongated, the expandable vents 114 are in their maximally closed position and maximally restrict the medium from communicating with its external environment.

It should be noted that the utilization of a single spring located on the top or bottom will suffice, but the dual spring approach creates more expandable vent housing travel, generates higher forces and is the preferred approach. It also should be noted that the expandable vent housing could also be the medium. The housing would be a multiplayer material as previously discussed and the medium would only be exposed on the inside of the expandable vent housing.

Figure 13A:
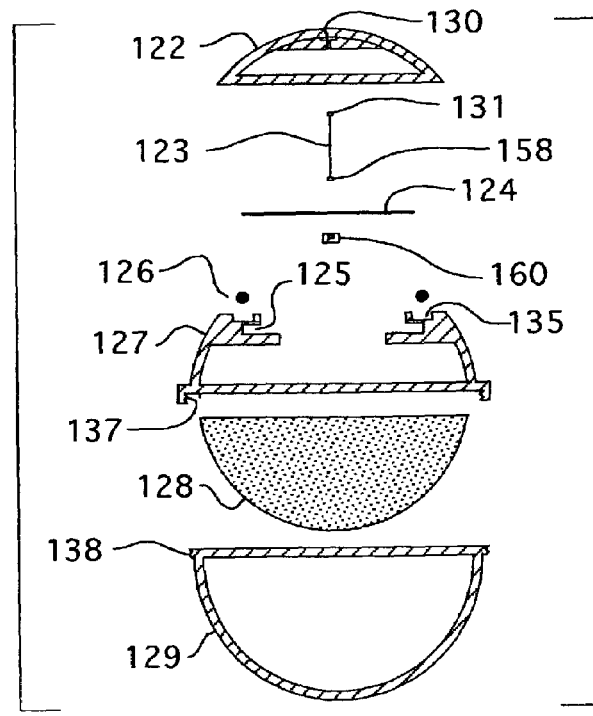
FIGS. 13A, 13B, and 13C depict a tenth preferred embodiment of the present invention in schematic representations, including an exploded sectional view and two sectional views thereof, respectively.
Figure 13B:
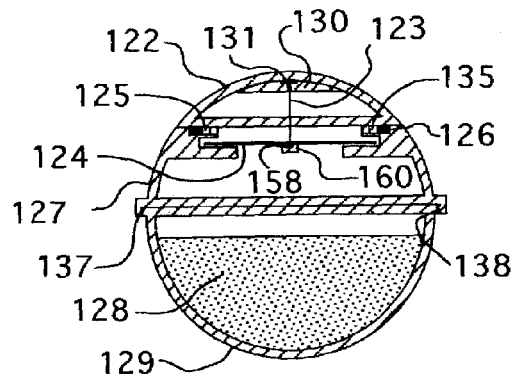
Figure 13C:
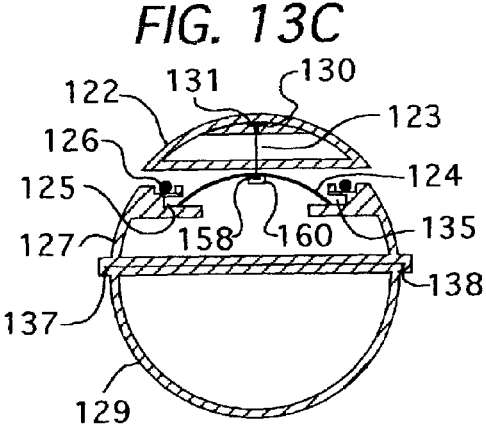

FIGS. 13A, 13B, and 13C illustrate a device that operates with a spring activated movable lid that allows the medium to communicate with its external environment within the useful range of its designed temperatures.

The device comprises a movable cap 122, a bimetallic spring 124, a spring connecting rod 123, a connecting rod spring retainer 160, and an upper housing 127 containing a spring retaining slot 125, a seal-retaining slot 132, a seal 126, and attachment threads 137. The device also includes a lower housing 129 containing attachment threads 138 as well as a medium 128.

The device is first assembled by inserting the spring connecting rod 123, through the bimetallic spring 124 and attaching the lower connecting rod attachment 158 to the connecting rod spring retainer 160. The upper spring connecting rod attachment 131 is inserted into the cap spring connecting rod retainer 130 and secured. The seal 126 is inserted into the seal-retaining slot 132 and the bimetallic spring 124 is inserted into spring retaining slot 125. This completes the assembly of the upper half of the housing 127. The medium 128 is placed into the lower housing 129. The assembly is complete and the device is ready for use when the upper housing 127 and lower housing 129 are screwed together via 137 and 138 and sealed.

In a preferred embodiment and using a complex liquid medium, FIG. 13B depicts the device operating at its minimally designed temperature. When the device is at its minimally designed temperature, the bimetallic spring 124 is fully contracted and pulling down on the cap 122 via the spring connecting rod 123. At this juncture, no medium 128 is in communication with its external environment.

FIG. 13C depicts the device operating at its maximally designed temperature. When the device is at its maximally designed temperature, the bimetallic spring 124 is fully expanded and has pushed the cap 122 off of the seal 126 to its full extent via the spring connecting rod 123. At this point, the medium is maximally communicating with its external environment.

FIGS. 14A–14F show a device almost identical to the device illustrated in FIGS. 3A–3E. The major exception is that the device in FIG. 14B uses a bimetallic spring 103 as the driving mechanism instead of a coiled spring.

The device is assembled by inserting and securing the bimetallic spring 103 into the static spring anchor 109 located on the post 108. The movable shutter 102, which includes vent holes 134, is installed by inserting the movable end of the bimetallic spring 102 into the movable spring anchor 105. The bimetallic spring 103 is installed properly when it rests against the bimetallic spring pivot 104. The movable shutter 102 is positioned and located concentrically with the lower housing 110 by placing the movable shutter 101 via the axis hole 250 onto the movable shutter rotation bearing 107. To complete the assembly, the upper shroud 101, which includes static vent holes 133, is attached to the lower housing 110 containing the medium 106.

Figure 14A:
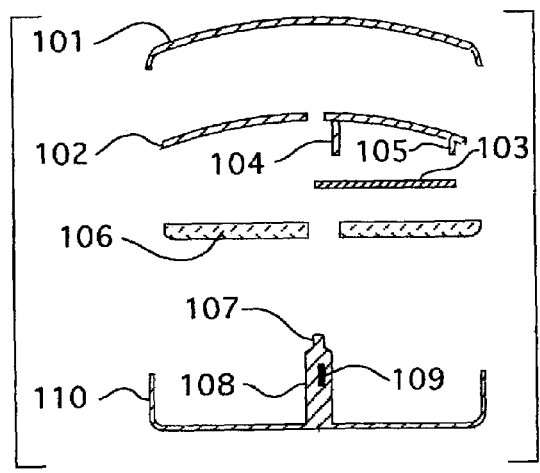
FIGS. 14A, 14B, 14C, 14D, 14E, and 14F schematically depict an eleventh preferred embodiment of the present invention, which is very closely related to the embodiment depicted in FIGS. 3A–3F.
Figure 14B:
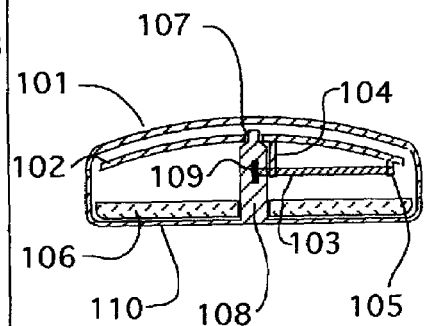
Figure 14C:
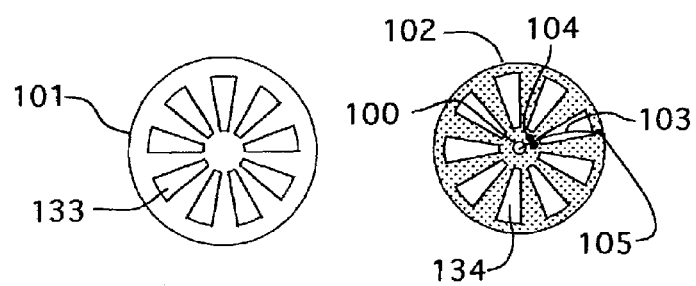
Figure 14D:
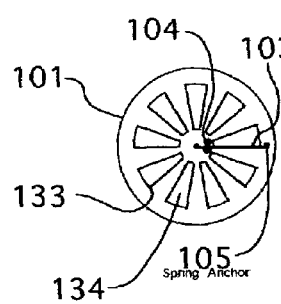
Figure 14E:
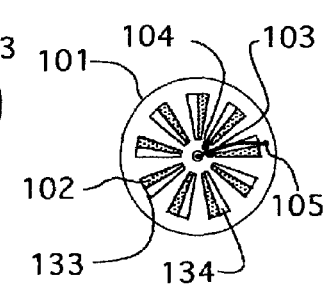
Figure 14F:
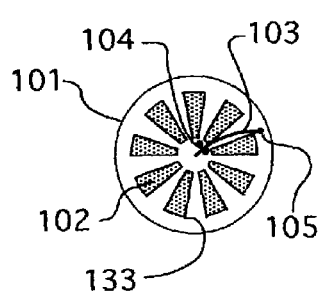

In a preferred embodiment the medium 106 is a fragrance gel. The sequence of operation is illustrated in FIG. 14D-14F. FIG. 14D illustrates the device at its minimally designed temperature. The movable shutter vents 134 are in total alignment with the static housing vents 133 and result in maximally exposing the medium to its external environment. The bimetallic spring 103 is contracted and appears linear.

FIG. 14E represents the device operating at increased ambient temperatures and illustrates the movable shutter vents 134 oriented to the static vents 133 in a configuration that allows the medium 106 to communicate to its external environment at only 50% of it maximal potential. At this stage, the bimetallic spring is partially expanded and bent or bowed. In essence, the static vents 133 are 50% blocked off.

FIG. 14F represents the device operating at its maximally designed temperature and illustrates the movable shutter vents 134 and the static vents 133 in total misalignment. At this stage, the bimetallic spring 103 is fully expanded and maximally bent and the medium 106 is maximally restricted from communicating with its external environment.

Figure 15A:
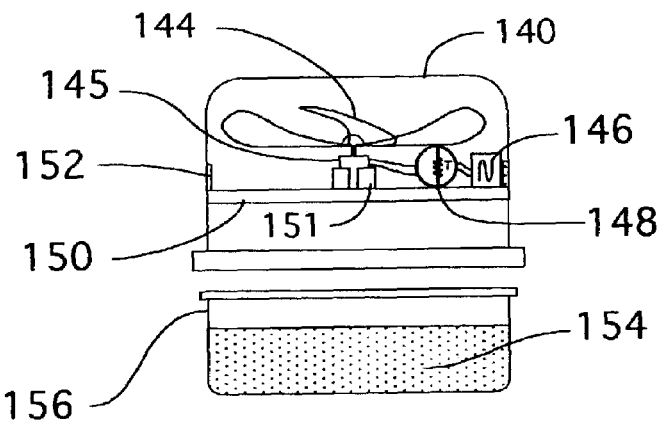
FIGS. 15A, 15B, and 15C depict a twelfth preferred embodiment of the present invention in schematic representations.
Figure 15B:
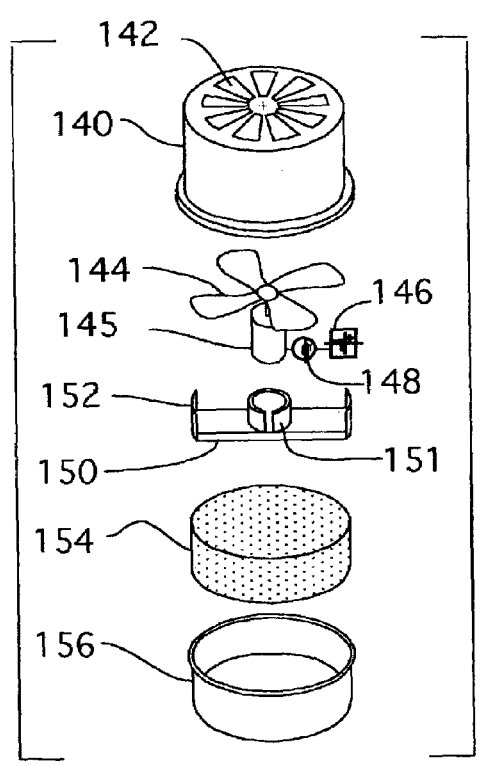
Figure 15C:
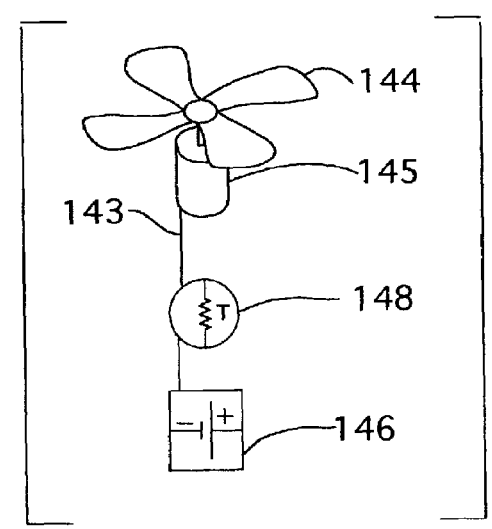

FIGS. 15A–15C illustrate a continually variable speed fan that changes fan speed with changes in ambient temperature. The fan comprises a fan motor 145, fan blade 144, a thermistor-type amperage controller 148 and a power source 146. The power source 146 is a battery, a 12-volt dc circuit or a household 120-volt circuit. An on-off switch is optional.

The device is assembled by initially inserting and securing the fan motor 145 and fan 144 into the fan retainer 151. The fan mounting bracket assembly consists of the mounting brackets 150; the mounting bracket mounts 152 and the fan retainer 151. The mounting bracket assembly and the fan are installed into the top housing via the mounting brackets 152 and secured. The medium reservoir 156, which contains the medium 154, is snapped into place with the top housing 140 and the device is ready for use.

In a preferred embodiment and using a fragrance as the medium 154, the device functions in the following manner. When the device is exposed to its highest designed ambient temperature, the thermistor control 148 operates at its maximum designed voltage resistance and causes the fan motor to operate at its lowest RPM or speed. This results in the medium communicating with its external environment in the most restricted manner. As the ambient temperature begins to decrease, the thermistor controller 148 continues to decrease its voltage resistance and allows the fan to continually increase in speed. At its minimally designed temperature, the fan motor receives full design voltage and the fan speed is maximized.

The result is that the medium's 158 communication with its environment is continually controlled and is perceived by the consumer as having constant effectiveness throughout its useful temperature range.

Figure 16A:
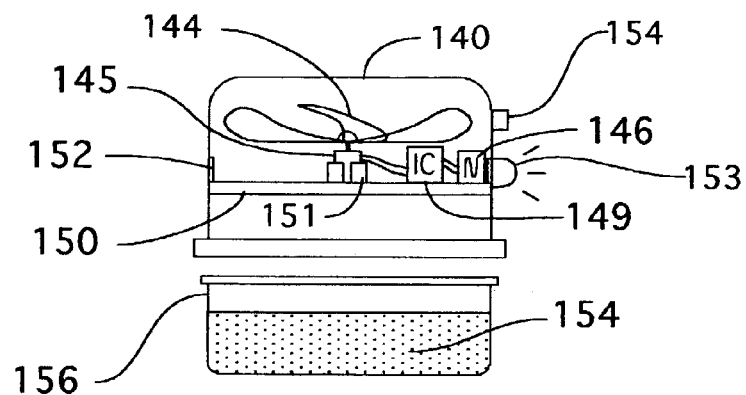
FIGS. 16A, 16B, and 16C schematically depict a thirteenth preferred embodiment of the present invention, which is very closely related to the embodiment depicted in FIGS. 15A–15F.
Figure 16B:
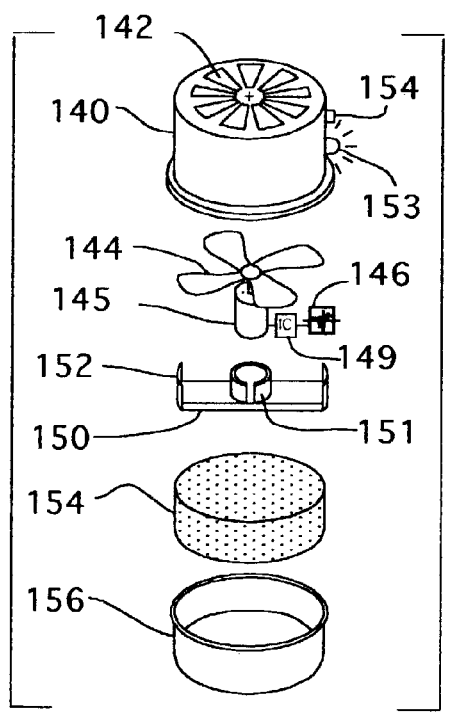
Figure 16C:
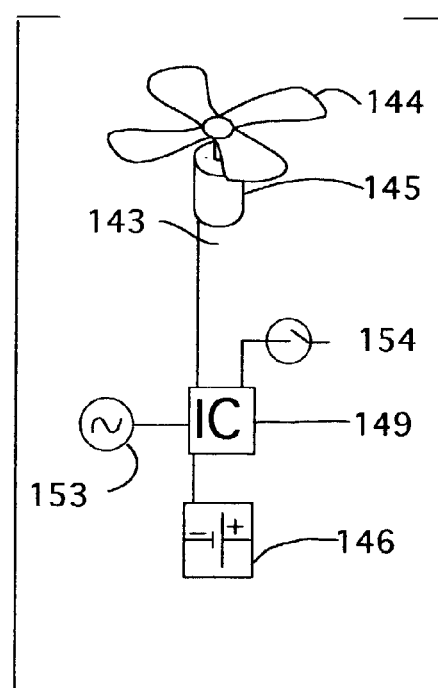

FIGS. 16A–16C represent a device identical in all aspects to the device in FIGS. 15, with the exception of the control circuitry 149. This device has an integrated circuit 149; a control circuit reset button 154 and an indicator light 153 that indicates when the useful life of the medium has expired. The device is assembled in the same manner as the device in FIG. 15.

In a preferred embodiment, this device is typically used in the home where the ambient temperatures are fairly stable. The medium 154 for this example is a fragrance gel. In a typical home, ambient temperatures vary very little in comparison to an automobile environment and as a result, compensating for large fluctuations in ambient temperature is not required. The devices previously described, to control the constant effectiveness of the medium in highly variable temperature environments, would not be the driving mechanisms of choice to accomplish this.

Assuming the household ambient temperatures are fairly constant, the major difficulty the device must compensate for is the decrease in vapor pressures and evaporation rates of the medium as it progresses through its useful life and ages. The lower vapor pressures and evaporation rates these mediums are characteristically known for as they age are counteracted by continually increasing the amount of airflow the medium is exposed to. This increases the evaporation rates of the medium as its vapor pressures naturally drop off in time and counteracts the effect. Many airflow movement devices can be used to programmably control the constant effectiveness of a medium to its external environment. Fans are members of the group consisting of airflow generators such as low frequency vibratory mechanisms, bellows, turbines, high frequency vibratory generators (piezoelectric), and turbines. Any of these mechanisms can be programmed accordingly and accomplish the same goal.

The device is designed and functions in the following manner. Once the chemical characteristics of the medium and its useful life have been defined, the integrated circuit is programmed for the application or product line. One or more variables can be programmed into the device and there are many parts and electric circuitry in the market one could use to accomplish the present invention which is being disclosed. However, the main goal of the present invention is to continuously control the pertinent variables of the device to maintain constant effectiveness of the medium to its external environment. These include time and temperature dependency, time versus airflow rate dependency, time versus medium exposure (evaporation or absorption) and time versus vibration profiles. High frequency vibration could also be used as a heater function. However, the following is a good straightforward description of a preferred embodiment. Two variables are programmed into the programmable circuit: time and voltage applied to the fan motor. The time variable is set using an internal programmable timer in the circuit, which would be typically designed to go through 360 degrees of counting to designate the useful life of the medium. In a straightforward programming example, 60 set points would characterize a medium that had a 60-day useful life and would represent 6 degrees of progression per day for 60 days on the clock. At this point, the timer would time out, send an electrical signal to the light 153 to turn on and then shut the control circuitry 149 off until the consumer pushed the reset button 154 to repeat the sequence of operation. This would be done when a new medium 154 was installed.

The voltage supplied 146 to the fan 145 is programmed in the same fashion and corresponds with the clock set points. When the entire programmable integrated circuit 149 is complete, a time versus fan speed profile is established.

To optimize the programmable circuit 149, the program would be written specific to the medium and optimize the constant effectiveness of the medium 154 to its external environment. It must be noted, that a myriad of profiles could be developed and many permutations are available.

Figure 17B:
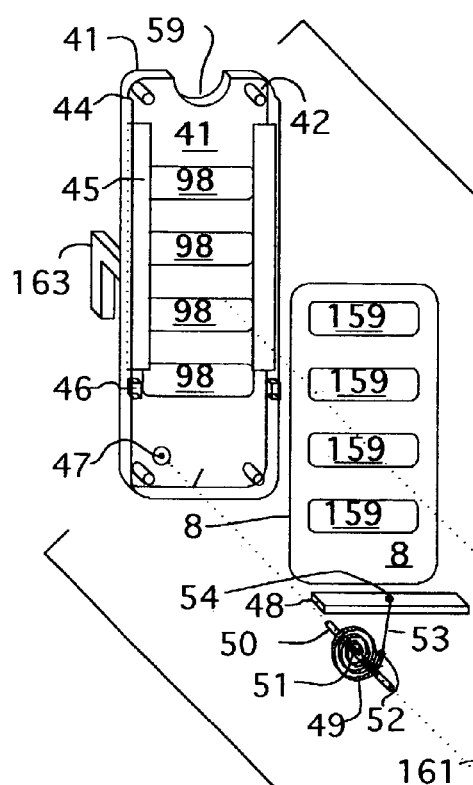
FIGS. 17A and 17B depict a fourteenth preferred embodiment of the present invention in schematic representations, including a perspective and exploded perspective view thereof, respectively.
Figure 17A:
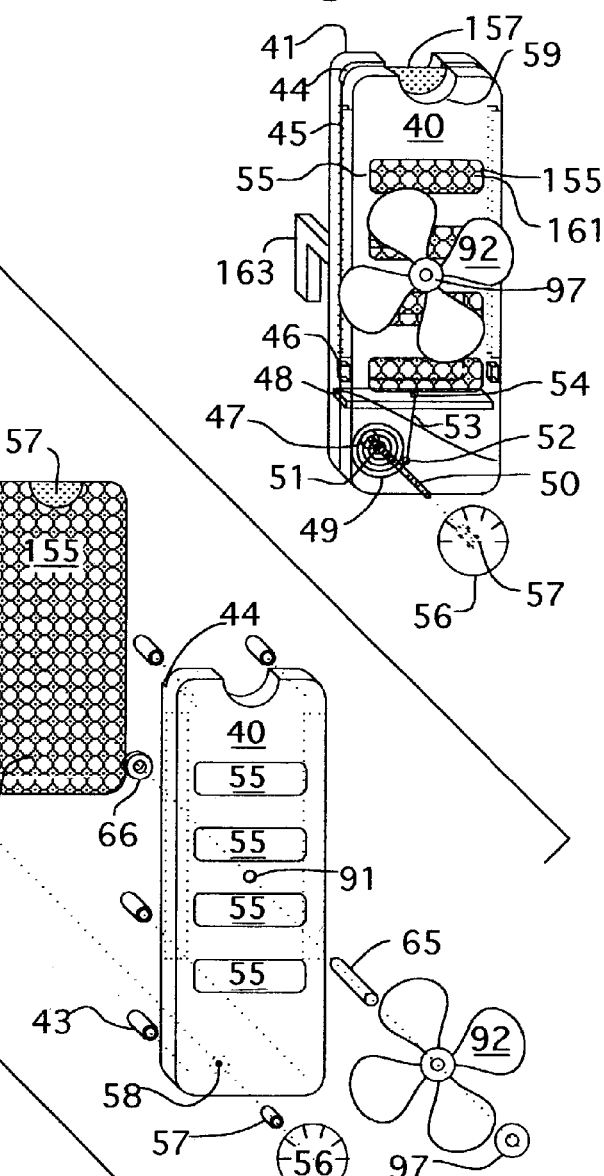

FIGS. 17A and 17B illustrate a device that identical in all aspects to FIGS. 6A and 6B with the exceptions of an added fan assembly, static vents 98 in the rear housing 41, a movable shutter 8, and a separate medium card 155. The device is also assembled in the same manner as FIGS. 6A and 6B with the exception of installing the added components of the fan assembly and the movable shutter 8.

The fan assembly is installed as follows. The fan axle 65 is inserted through the fan hole 162 and secured with the fan blade retainer 97. The fan axle 65 is now inserted through the fan axle-receiving hole 91 and secured with the fan axle retainer 66. The rest of the device is installed in the same manner as described in the verbiage for device in FIGS. 6A and 6B.

The movable shutter is installed by inserting it through the slot 44 until it comes to rest on the shutter platform 48. The shutter 8 is located closest to the rear housing 41.

The medium card 155 is also inserted into slot 44 and comes to rest on the platform stop 49. The medium card 155 is stationary and located closest to the front housing 40.

In a preferred embodiment, fragrance is used as the medium. The device is attached to the automobile air vent housing by the auto vent attachment 163. The device controls the exposure of the medium to its external environment by controlling the rate of airflow delivered by the auto vent through and around the device. The volume of airflow allowed through the static vents 55 and 98, movable shutter vents 159, the speed of the device's fan 92 and around the periphery of the device, are all used to accomplish this. The airflow around the periphery of the device also helps control the speed of fan 92. The fan speed is the highest when the auto vent air is cold and the vent system is unrestricted and the fan speed is the slowest when the auto vent air is hot and the vent system is restricted.

The reason why this device is so advantageous to the consumer is that it discriminates between hot air and cold air coming out of the automobile's vent system (summer versus winter). When hot air is coming out of the automobile's vent system, the spring 49 expands and moves the shutter vents 159, via the platform 48, to positions where the shutter vents 159 become misaligned with the static vents 98 and 55 and retard airflow through the device and fan 92. This is consistent with what has been discussed; with an evaporative medium 155, we decrease the exposure of the medium 155 to its external environment when the ambient temperature is hot to prevent an overpowering perception of the fragrance to the consumer and increase exposure of the medium 155 to its environment when it is cold, to increase the strength of a weak and ineffective perception of the fragrance to the consumer.

This counteracts the changes in vapor pressures and evaporation rates with changing temperatures and maintains constant effectiveness of the medium 155 as it communicates with its external environment.

Figure 18A:
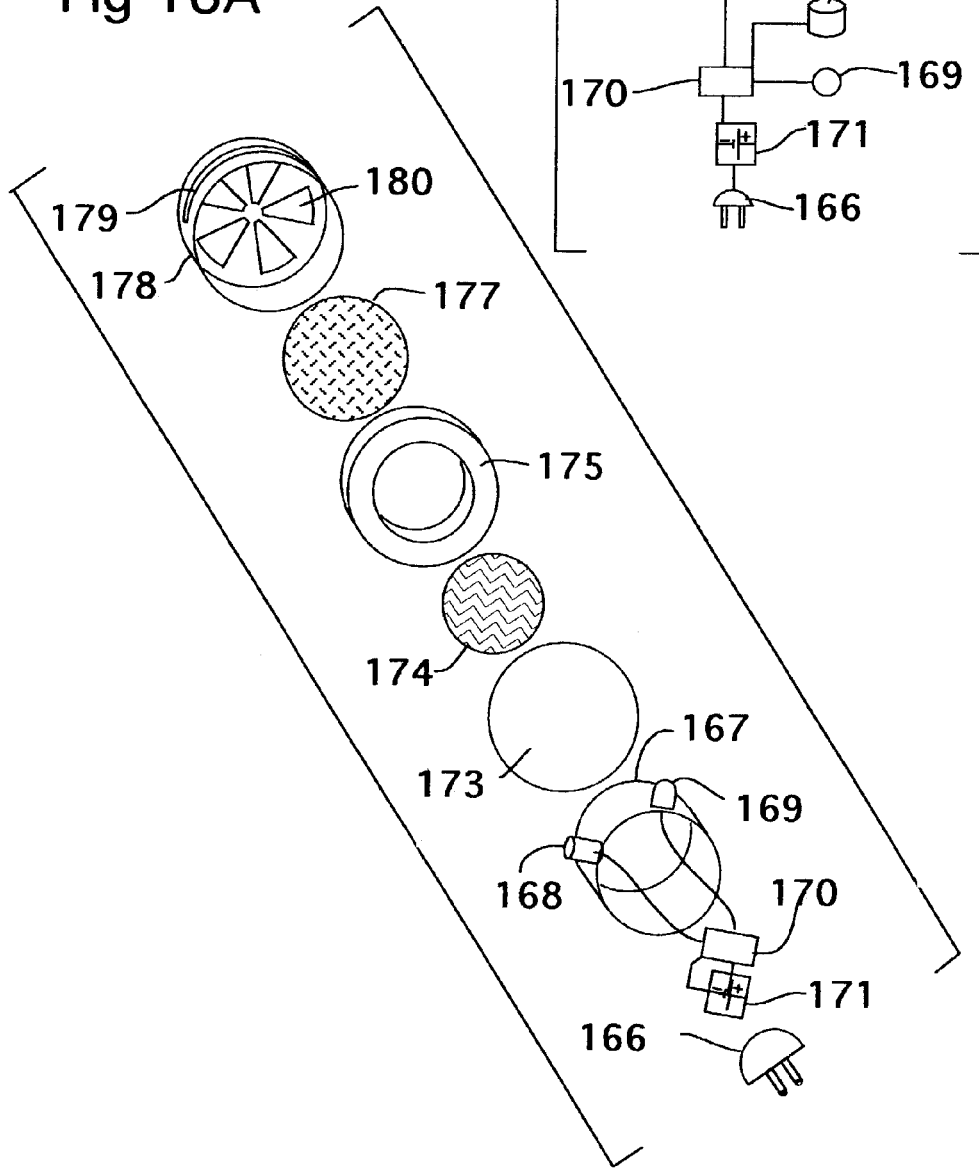
FIGS. 18A and 18B depict a fifteenth preferred embodiment of the present invention in schematic representations, including an exploded view and a detailed view of some of the components thereof, respectively.
Figure 18B:
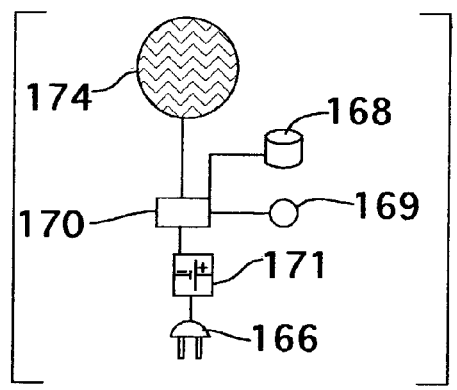

FIG. 18A illustrates a breakout of a programmable heating device to control the constant effectiveness of a medium to its surrounding environment. The heating device is an electrical resistive heater and is a member of the group of heaters comprising induction heaters and high frequency vibratory heaters such as piezoelectric heaters. Any of these members can be used for the heating device and programmed accordingly.

The device is assembled in the following manner. The following components are installed in the base housing 167; the use up light 169, the reset button 168, the programmable circuitry 170, the power source regulator 171, the power source plug 166, the heat shield 173, the heater 174 and the heater/medium separator 175. The upper housing 178 which comprises the static vents 180 and the medium slot 179 is snapped into place onto the base housing 167 and the device is assembled and ready for use once the medium 177 is inserted into the medium slot 179 and the device is plugged in.

In a preferred embodiment, this device is typically used in the home where the ambient temperatures are fairly stable. The medium 177 for this example is a fragrance gel. Assuming the household ambient temperatures are fairly constant, the major difficulty the device must compensate for is the decrease in vapor pressures and evaporation rates of the medium as it progresses through its useful life and ages. The lower vapor pressures and evaporation rates these mediums 177 are characteristically known for as they age, are counteracted by continually increasing the amount of heat the medium 177 is exposed to. This increases the evaporation rates of the medium 177 as its vapor pressures naturally drop off in time and counteracts the effect. Many heating devices can be used to programmably control the constant effectiveness of a medium to its external environment. They were discussed earlier.

The device is programmed in the same manner and using the same concepts that were described device in FIGS. 16A–16C. The major exception is that we are using a heating mechanism for this application instead of a fan.

In this example, two variables are programmed into the programmable circuit 170: time and voltage applied to the heater. The time variable is set using an internal programmable timer in the circuit, which would be typically designed to go through 360 degrees of counting to designate the useful life of the medium. In a straightforward programming example, 60 set points would characterize a medium that had a 60-day useful life and would represent 6 degrees of progression per day for 60 days on the clock. At this point, the timer would time out, send an electrical signal to the light 169 to turn on and then shut the control circuitry 170 off until the consumer pushed the reset button 168 to repeat the sequence of operation. This would be done when a new medium 177 was installed.

The voltage supplied 166 to the heater 174 is programmed in the same fashion and corresponds with the clock set points. When the entire programmable integrated circuit 170 is complete, a time versus heater temperature profile is established.

To optimize the programmable circuit 170, the program would be written specific to the medium 177 and optimize the constant effectiveness of the medium 177 to its external environment. It must be noted, that a myriad of profiles could be developed and any permutations are available. They do not have to be linear and most often are not.

The devices in FIGS. 19A–19D illustrate a novel automatic thermostatic ratchet mechanism to control the exposure of a medium 250 to its external environment. The device comprises a housing assembly, a thermal response housing assembly FIG. 20A at 205, a latch notch assembly 210, and a latch housing assembly 213.

The housing assembly consists of a housing 252, a manual id 254, a lid hinge 258, a latch retainer slot 260, and a keyway slot 260.

Figure 20A:
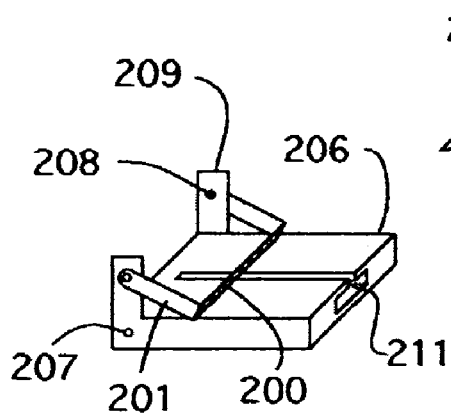
FIGS. 20A and 20B depict a thermal response housing assembly, which is a component of the embodiment of FIGS. 19A–19D.
Figure 20B:
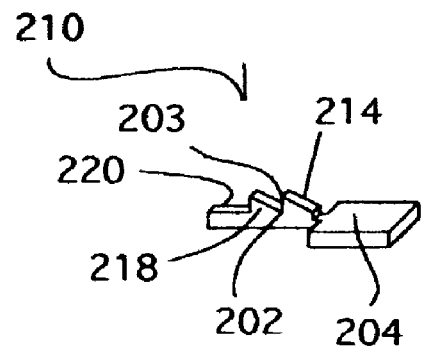
Figure 20C:
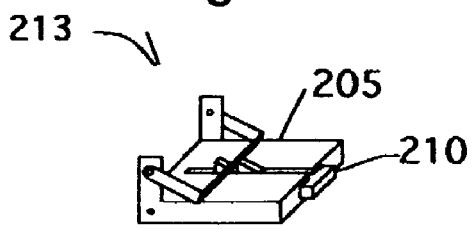

The thermal response housing assembly in FIG. 20A at 205 comprises a latch guide housing 206, a latch guide slot 211, a swing arm bracket 209, a swing arm pivot 208, a housing pivot 207, and a bimetallic spring 200. FIG. 20B illustrates the latch notch assembly 210 and comprises a latch 204 and a ratchet tooth 218, which includes a notch 202, an incline 214, and a peak 203.

Figure 19A:
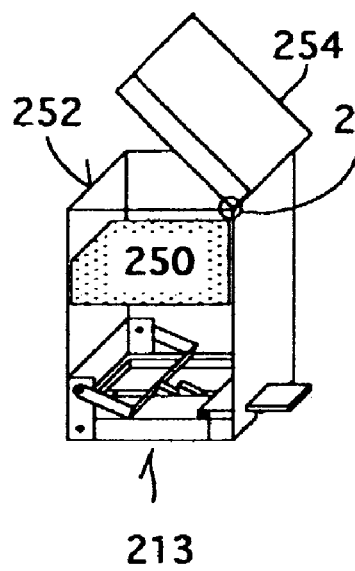
FIGS. 19A, 19B, 19C depict a sixteenth preferred embodiment of the present invention in schematic representations.
Figure 19B:
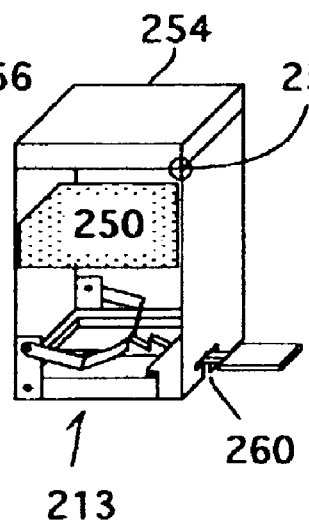
Figure 19C:
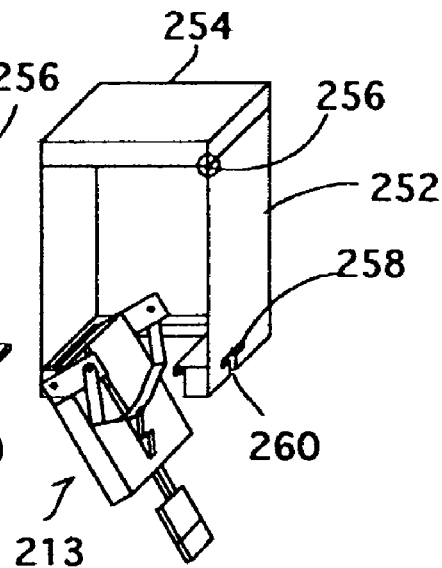

FIGS. 19A–19D illustrate in a simplistic way, the basic sequence of operations. FIG. 19A illustrates the device in the cold condition with the medium 250 loaded into the housing 252. FIG. 19B illustrates the device in the hot position and FIG. 19C illustrates the device in the final stage of allowing the medium 250 to communicate with its external environment.

FIGS. 21A–21E illustrates the sequence of operations. Its sole control mechanism resides in the movements of the thermal response latch assembly 213.

In a preferred embodiment, the medium 600 will be a dishwashing detergent and the device will go through a hot, cold, and hot cycle before the medium 600 is dispensed. FIG. 21A depicts a thermal response latch assembly 213 in the first phase of the sequence. The external environment in this phase is cold and the bimetallic spring 200 is contracted, located between the two ratchets 218 and its pivot 208 is in the fully down position. As the temperature rises, the bimetallic spring 200 starts to expand, bow, and push the ratchet 218 forward. As the ratchet 218 is being pushed forward, the latch 204 is simultaneously being pushed forward because it is an integral part of the latch notch assembly 213. When the external environment reaches its maximum temperature, the bimetallic spring 200 is fully expanded, and pushes the ratchet 218 to its farthest position forward. This is depicted in FIG. 21B.

Phase two begins when the temperature of the external environment begins to decrease. The decrease in temperature causes the bimetallic spring 200 to contract, pull back, and ride up on the incline of the ratchet 214 until the spring 200 reaches the peak of the ratchet 203. At nearly full contraction, the spring 200 drops down into the second ratchet notch 202. The ability of the spring 200 to ride up the ratchet incline 214 and drop back into the ratchet notch 202 is created by the bimetallic spring arm pivot 208. At this juncture, we have completed one hot to cold cycle.

The latch housing assembly 213 goes through another hot to cold cycle as previously discussed. However, when the temperature gets hot in this cycle and the spring 200 has pushed the second ratchet tooth 218 as far as the expansion of the spring 200 will allow, it dispenses its medium 250 to the external environment. This occurs when the latch retainer slot 258 no longer retains the latch. This happens because the distance the latch 204 has traveled in the second cycle has caused the latch 204 to be pushed out so far that it loses support from the latch retainer slot 258 in the housing 252. The ratchet arm 220 width is so much narrower than the latch 204 that is passes right through the latch retainer slot 258 via the key way 260. This allows the latch assembly 213 to drop via the housing pivot 207 and dispense the medium 250 to its external environment.

FIGS. 21A–21D work in a very similar manner to the first device with the exception that this device dispenses its medium 250 on the first cycle hot and uses a method whereby the bimetallic spring 200 pulls the latch notch assembly 210, instead of pushing it. In addition, only one ratchet tooth 218 is used. There are no new parts in this device; the system just functions differently.

FIG. 21A illustrates the device in the start up or cold environmental condition. Please note that the spring's 200 starting position is resting on the peak of the ratchet tooth 218. As the dishwashing temperature gets progressively hotter, the spring 200 expands and progresses down the ratchet incline 214. As the spring 200 expands to its full extent, it falls into the ratchet notch 202. This is illustrated in FIG. 21B. As the temperature in the wash cycle decreases, the spring 200 contracts and pulls the ratchet notch assembly 210 backwards. Once the proper design temperature is reached, the latch retainer slot 258 no longer supports the latch 204 and the medium 250 is exposed to its external environment. This is illustrated in FIG. 21D.

FIGS. 22A–23C illustrate a device similar in all aspects to the embodiment presented immediately above with the exception that it may be used to either transform medium 250 from the top medium chamber to the bottom when desired, or holds two media 250 and 251 simultaneously in separate compartments until the external environments temperature is met, to allow the two to be mixed when needed. This is done by dumping the top chamber contents into the bottom chamber prior to releasing the combined ingredients to their external environment simultaneously.

I claim:

1. A device for automatically controlling the interaction of a medium with the external environment the temperature of which varies or remains constant, the device comprising the following elements, which interact to form an independent, unitary apparatus:

a medium;

a means for providing constant effectiveness of the medium in the external environment; and an automatic drive mechanism communicating with, and driving, and continually adjusting the means for providing constant effectiveness of the medium in the external environment, so that a desired interaction of the medium with the external environment is afforded.

2. The device of claim 1, wherein the medium is a member selected from the group consisting of temperature-sensitive media, moisture-sensitive media, chemically-reactive media, evaporative media, and absorptive media.

3. The device of claim 2, wherein the medium is a member selected from the group consisting of liquids, solids, gases, fibers, gels, and encapsulated materials.

4. The device of claim 3, which additionally comprises a means for containing the medium.

5. The device of claim 4, wherein the means for containing the medium is a receptacle for the medium.

6. The device of claim 1, wherein the means for providing constant effectiveness of the medium in the external environment incorporates a cooperating means for presenting an on/off condition at chosen levels of exposure of the medium to the external environment.

7. The device of claim 5, which additionally comprises a housing for the receptacle for the medium, the housing incorporating the means for providing constant effectiveness of the medium in the external environment.

8. The device of claim 7, wherein the means for providing constant effectiveness of the medium in the external environment is a movable vent.

9. The device of claim 7, wherein the means for providing constant effectiveness of the medium in the external environment is an expandable vent.

10. The device of claim 8, wherein the movable vent is a member selected from the group consisting of movable shutters, movable louvers, movable orifices, and movable sheaths.

11. The device of claim 7, wherein the automatic drive mechanism is a member selected from the group consisting of temperature-responsive members and temperature-responsive fluid movement devices.

12. The device of claim 11, wherein the temperature-responsive member manifests variations in the surface area thereof as the temperature thereof is varied.

13. The device of claim 12, wherein the temperature-responsive member is a member selected from the group consisting of linear springs, spiral metallic springs, multimetallic springs, polymeric springs, and pop springs.

14. The device of claim 8, which additionally comprises a static vent, which is securely positioned within the housing in substantial alignment with the movable ventiduct, the movable vent being driven by the automatic drive mechanism to move relative to the static vent, so that constant effectiveness of the medium in the external environment is provided.

15. The device of claim 14, wherein the static vent is a member selected from the group consisting of static orifices, static louvers, and static sheaths.

16. The device of claim 14, wherein the movable vent and the static vent have essentially the same geometrical shapes, so that the constant effectiveness of the medium in the external environment is provided in a substantially linear fashion.

17. The device of claim 14, wherein the movable vent and the static vent have essentially different geometrical shapes, so that the constant effectiveness of the medium is the external environment is provided in a substantially non-linear fashion.

18. The device of claim 1, which additionally comprises a means for inducing a temperature change in the medium.

19. The device of claim 18, wherein the means for inducing a temperature change in the medium is a programmable heater.

20. The device of claim 19, wherein the programmable heater is a member selected from the group consisting of thermal profile generators and time/temperature thermal profile generators.

21. The device of claim 19, which additionally comprises a means cooperating with the programmable heater for providing a signal evincing the end of a programmed cycle.

22. The device of claim 12, wherein the housing comprises a front face and a back face which are joined together to form a slot therebetween, the slot functioning as the reservoir for the medium; the medium being in the form of a sheet which has two major surfaces and which is configured to fit within the slot and to be capable of movement therein; at least one of the front face and the back face of the housing having at least one fixed vent therein; the temperature-responsive member being connected to a means for holding the medium and moving the medium within the slot as a result of changes in temperature, so that the medium is oriented with respect to the at least one vent for communication therethrough with the external environment; the major surfaces of the medium having at least one masked area and at least one unmasked area thereon, the at least one masked area and the at least one unmasked area each having substantially the same shape and surface area as the at least one fixed vent; the at least one masked area being in substantial alignment with the at least one fixed vent when the external environment is at a first temperature, and the at least one unmasked area being in substantial alignment with the at least one fixed vent when the external environment is at a second temperature, the first temperature being higher than the second temperature.

23. The device of claim 7, which additionally comprises a means for inducting air currents across the medium contained in the receptacle.

24. The device of claim 23, wherein the means for inducing air currents across the medium contained in the receptacle is a fan which is programmed for continuous operation at a substantially constant blade speed.

25. The device of claim 23, wherein the means for inducing air currents across the medium contained in the receptacle is a fan, the blade speed of which is controlled by the automatic drive mechanism.

26. The device of claim 13, wherein the housing comprises a first concave face and a second concave face, which faces when joined together form an integral, hollow enclosure, the first concave face and the second concave face being connected to each other at one area on one edge thereof by means of a hinge, the second concave face containing the medium therein, and the automatic drive mechanism being a bimetallic spring, which is attached to the first concave face and the second concave face, respectively, in the vicinity of the hinge, so that the first concave face and the second concave face are positioned apart to expose the medium to the external environment when the external environment is at a first temperature, and the first concave face and the second concave face are drawn together to form an integral hollow enclosure when the external environment is at a second temperature, the first temperature being lower than the second temperature.

27. The device of claim 13, wherein the external environment is a liquid, and wherein the medium is a member selected from the group consisting of liquids and powders, and wherein the device additionally comprises a means for automatically dispensing the medium from the receptacle into the liquid external environment, the means for automatically dispensing the medium from the receptacle into the liquid external environment being driven by the automatic drive mechanism.

* * * * *